(12) United States Patent
Andrews et al.

(10) Patent No.: US 7,393,870 B2
(45) Date of Patent: Jul. 1, 2008

(54) **3-(HETEROARYLAMINO)METHYLENE-1,
3-DIHYDRO-2H-INDOL-2-ONES AS KINASE
INHIBITORS**

(75) Inventors: Steven W. Andrews, Longmont, CO
(US); Julie A. Wurster, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/282,044

(22) Filed: Nov. 17, 2005

(65) Prior Publication Data

US 2006/0074116 A1 Apr. 6, 2006

Related U.S. Application Data

(62) Division of application No. 10/256,381, filed on Sep. 26, 2002, now Pat. No. 7,005,444.

(60) Provisional application No. 60/325,816, filed on Sep. 27, 2001, provisional application No. 60/325,817, filed on Sep. 27, 2001.

(51) Int. Cl.
*A61K 31/422* (2006.01)
*C07D 413/12* (2006.01)
(52) U.S. Cl. .................................. 514/378; 548/247
(58) Field of Classification Search ................ 548/247; 514/378
See application file for complete search history.

(56) References Cited

U.S. PATENT DOCUMENTS

| | | | |
|---|---|---|---|
| 4,966,849 A | 10/1990 | Vallee et al. |
| 5,217,999 A | 6/1993 | Levitzki et al. |
| 5,302,606 A | 4/1994 | Spada et al. |
| 5,330,992 A | 7/1994 | Eissenstat et al. |
| 5,792,783 A | 8/1998 | Tang et al. |
| 5,834,504 A | 11/1998 | Tang et al. |
| 5,883,113 A | 3/1999 | Tang et al. |
| 5,883,116 A | 3/1999 | Tang et al. |
| 5,886,020 A | 3/1999 | Tang et al. |
| 6,316,635 B1 | 11/2001 | Tang et al. |

FOREIGN PATENT DOCUMENTS

| | | |
|---|---|---|
| DE | 19924401 A1 | 11/2000 |
| WO | 91/15495 | 10/1991 |
| WO | 92/20642 | 11/1992 |
| WO | 92/21660 | 12/1992 |
| WO | 94/03427 | 2/1994 |
| WO | 94/10202 | 5/1994 |
| WO | 94/14808 | 7/1994 |
| WO | WO 00/12084 | 3/2000 |
| WO | WO 00/56710 | 9/2000 |

OTHER PUBLICATIONS

Science (1999), vol. 286, 531-537.*
Cancer and Metastasis Reviews (1998), 17(1), 91-106.*
Plowman et al, "Receptor Tyrosine Kinases as Targets for Drug Intervention", DN&P 7(6) Aug. 1994: 334-339.
Bolen, "Nonreceptor tyrosine protein kinases", Oncogen 8: 2025-2031,1993.
Kendall et al, "Inhibition of vascular endothelial cell growth factor activity by an endogenously encoded soluble receptor", Proc. Nat'l Acad. Sci 90: 10705-09,1994.
Kim et al, Inhibition of vascular endothelial growth factor-induced angiogenesis suppresses tumour growth in vivo, Nature 362: 841-844,1993.
Jellinek et al, "Inhibition of Receptor Binding by High-Affinity RNA Ligands to Vascular Endothelial Growth Factor", Biochemistry 33: 10450-56, (1994).
Takano et al, "Inhibition of Angiogenesis by a Novel Diaminoanthraquinone that Inhibits Protein Kinase", Mol. Bio. Cell 4: 358A,1992.
Kinsella et al, "Protein Kinase C Regulates Endothelial Cell Tube Formation on Basement Membrane Matrix, Matrigel", Exp. Cell Res. 199: 56-62,1992.
Wright et al, "Inhibition of Angiogenesis In Vitro and In Ovo With an Inhibitor of Cellular Protein Kinases, MDL 27032", J. Cellular Phys. 152: 448-57,1992.
Mariani et al, "Inhibition of angiogenesis by FCE 26806, a potent tyrosine kinase inhibitor", Proc. Am. Assoc. Cancer Res. 35: 2268,1994.
Castro et al , "Quantitative Image Analysis of Laser-induced Choroidal Neovascularization in Rat", Exp. Eye Res. 2000; 71:523-55.
McMurry, John, Organic Chemistry Fifth Edition, Brooks/Cole, (2000), p. 198.
Hasan et al, VEGF antagonists, Expert Opin. Biol. Ther. (2001) 1(4):703-718.

* cited by examiner

*Primary Examiner*—Rebecca L Anderson
(74) *Attorney, Agent, or Firm*—Joel B. German; Dean G. Stathakis; Martin A. Voet

(57) ABSTRACT

The present invention relates to organic molecules capable of modulating tyrosine kinase signal transduction in order to regulate, modulate and/or inhibit abnormal cell proliferation.

2 Claims, No Drawings

3-(HETEROARYLAMINO)METHYLENE-1,3-DIHYDRO-2H-INDOL-2-ONES AS KINASE INHIBITORS

This application is a divisional of Ser. No. 10/256,381, filed Sep. 26, 2002, now U.S. Pat. No. 7,005,444, which claims priority under 35 U.S.C. § 119(e)(1) to provisional application Nos. 60/325,816 and 60/325,817, filed Sep. 27, 2001.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles.

These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phophorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR—R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci 90: 10705-09; Kim, et al, 1993, Nature 362: 841-844), RNA ligands (Jellinek, et al, Biochemistry 33: 10450-56); Takano, et al, 1993, Mol. Bio. Cell 4:358A; Kinsella, et al, 1992, Exp. Cell Res. 199: 56-62; Wright, et al, 1992, J. Cellular Phys. 152: 448-57) and tyrosine kinase inhibitors (PCT Application Nos. WO 94/03427; WO 92/21660; WO 91/15495; WO 94/14808; U.S. Pat. No. 5,330, 992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinylene-azaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302, 606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Finally, certain small compounds are disclosed in U.S. Pat. Nos. 5,792,783; 5,834,504; 5,883,113; 5,883,116 and 5,886, 020 as useful for the treatment of diseases related to unregulated TKS transduction. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

In one illustrative embodiment, the compounds of the present invention have the following general formula I:

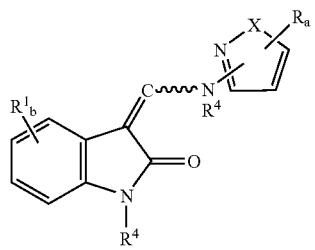

wherein $R^1$ is selected from the group consisting of halogen and $C_1$ to $C_4$ alkyl; X is selected from the group consisting of $NR^3$ and O; R is selected from the group consisting of $C_1$ to $C_6$ alkyl,

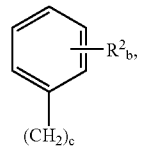

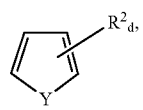

halogen, cyano, $SR^3$, $COOR^3$, $C(CH_3)=CH-C(CH_3)=N$ and $FC=CH-CH=CH$;

Y is selected from the group consisting of O and S; $R^2$ is selected from the group consisting of $R^3$, $OR^3$, $C(O)OR^3$ and $N(R^3)_2$; a is 0 or an integer of from 1 to 2; b is 0 or an integer of from 1 to 3; c is 0 or an integer of from 1 to 2; d is an integer of from 1 to 3; $R^3$ is selected from the group consisting of H, $C_1$ to $C_8$ alkyl, benzyl dialkylaminoalkyl, N-methyl-piperazinylalkyl and morpholinylalkyl; $R^4$ is selected from the group consisting of H, $C_1$ to $C_8$ alkyl and phenyl; the wavy line represents a E or Z bond and pharmaceutically acceptable salts thereof.

DETAILED DESCRIPTION OF THE INVENTION

In one embodiment of the present invention $R^1$ is selected from the group consisting of H, i.e. b is 0; $CH_3$, F and Cl.

Preferably X is NH.
Preferably $R^4$ is H.
Preferably Y is O.
Preferably c is 0 or 1.

R is preferably selected from the group consisting of phenyl, p-methylphenyl, furyl, p-methoxybenzyl, t-butyl, methyl, 3-(2-methyl-5-t-butyl)furyl, m-methoxyphenyl and p-dimethylaminophenyl.

More preferably when b is 0 and X is NH, R is selected from the group consisting of phenyl, methylphenyl, furanyl, methoxybenzyl, t-butyl, methoxyphenyl and methyl.

More preferably, when b is 0 and X is O, R is selected from the group consisting of methyl and tertiary butyl.

More preferably, when b is 1, $R^1$ is $CH_3$ and X is NH or $R^1$ is Cl and X is NH. In such instances a may preferably be 0.

When b is 1, $R^1$ is $CH_3$ and X is NH,
R may be selected from the group consisting of furanyl and phenyl.

When b is 1, $R^1$ is Cl and X is NH,
R may be furanyl

When b is 1, $R^1$ is F, R may be selected from the group consisting of methyl and furyl.

It is noted that R may also represent a condensed ring that is attached to the above heterocyclic ring at two positions. For example, as shown in Example 15, below, $CF=CH-CH=CH$ may be attached at the 4 and 5 positions of the pyrazole ring.

In particular, the compounds of the present invention are selected from the compounds of Table 1, below.

Unsubstituted, 4-methyl, 5-Chloro & 5-Fluoro
3-[(Substituted pyrazoyl-amino)-methylene]-1,3-
dihydro-indol-2-ones

| Example # | R¹ | R Substitution 4 | 5 |
|---|---|---|---|
| 1 | H | H | H |
| 2 | H | H | Ph |
| 3 | H | H | p-MePh |
| 4 | H | H | 2-Furyl |
| 5 | H | H | CH₂(p-MeO)Ph |
| 6 | 4'-Me | H | H |
| 7 | 4'-Me | H | 2-Furyl |
| 8 | 4'-Me | H | Ph |
| 9 | 5'-Cl | H | H |
| 10 | 5'-Cl | H | 2-Furyl |
| 11 | H | Br | Ph |
| 12 | 4'-Me | Br | Ph |
| 13 | 5'-Cl | Br | Pb |
| 14 | 5'-Cl | H | Ph |
| 15 | H | —CF=CH—CH=CH— | |
| 17 | H | CO₂Et | H |
| 18 | H | CN | SMe |
| 19 | H | CO₂H | H |
| 20 | H | CN | H |
| 21 | H | Br | H |
| 22 | H | H | t-Bu |
| 23 | H | H | Me |
| 24 | H | H | 4-carbomethoxyphenyl |
| 25 | H | —C(Me)=CH—C(Me)=N— | |
| 26 | 5'-F | H | Me |
| 27 | 5'-F | H | 2-Furyl |

Unsubstituted, 4-methyl, 5-Chloro & 5-Fluoro
3-[(Substituted pyrazoyl-amino)-methylene]-1,3-
dihydro-indol-2-ones

| Example # | R¹ | R Substitution 4 | 5 |
|---|---|---|---|
| 16 | H | (3,4-Dimethoxy)-phenyl | Me |

| Example # | R¹ | R Substitution 4 | 5 |
|---|---|---|---|
| 28 | 5'-F | H | 3-(2-Methyl-5-t-Butyl)-Furyl |
| 29 | H | H | 3-(2-Methyl-5-t-Butyl)-Furyl |
| 30 | H | H | p-Methoxyphenyl |
| 31 | H | H | 3,5-bis(Benzyloxy)-phenyl |
| 32 | H | H | 3,5-(Dimethyl)-phenyl |
| 33 | H | H | m-Methoxyphenyl |
| 34 | H | H | 2,4-(Dimethyl)phenyl |
| 35 | H | H | p-(Dimethylamino)-phenyl |
| 36 | H | H | —CH₂-[(2,3,5-trimethyl)-phenyl] |
| 37 | H | H | o-Methoxyphenyl |
| 38 | H | H | p-Ethoxyphenyl |
| 39 | H | H | —CH₂-(m-tolyl) |
| 40 | H | H | —CH₂Ph |

3-[(Substituted heteroaryl-amino)-methylene]-1,3-
dihydro-indol-2-ones

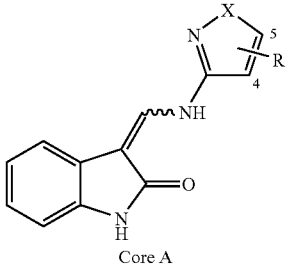

Core A

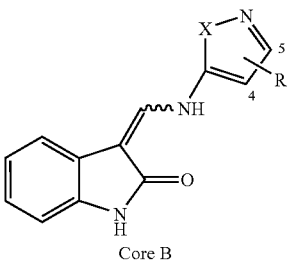

Core B

| Example # | Core | X | R Substitution 4 | 5 |
|---|---|---|---|---|
| 41 | A | O | H | t-Bu |
| 42 | A | O | Br | Me |
| 43 | A | O | H | H |
| 44 | A | O | H | Me |
| 45 | B | O | Me | Me |
| 46 | B | NEt | H | H |
| 47 | B | NMe | H | 3-(2-Methyl-5-t-Butyl)-Furyl |

Unsubstituted, 4-methyl & 6-Fluoro 3-[(Substituted heteroaryl-amino)-methylene]-1,3-dihydro-indol-2-ones
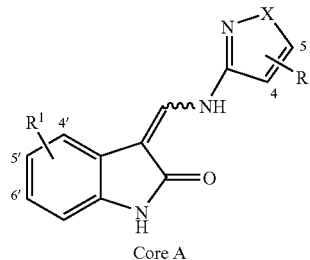
Core A
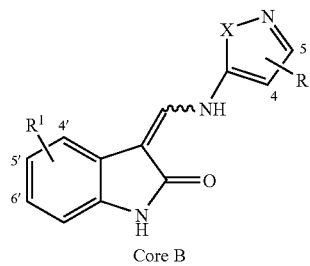
Core B
| | | | | | R Substitution |
|---|---|---|---|---|---|
| Example # | Core | $R^1$ | X | 4 | 5 |
| 48 | A | 6'-F | O | H | Me |
| 49 | A | 6'-F | NH | H | Me |
| 50 | A | 6'-F | NH | H | 2-Furyl |
| 51 | A | 6'-F | NH | H | phenyl |
| 52 | B | 6'-F | NH | H | 3-(2-Methyl-5-t-Butyl)-Furyl |
| 53 | A | 6'-F | NH | H | H |
| 54 | B | 4'-Me | NH | H | $CH_2$(p-MeO)Ph |
| 55 | B | 6'F | NH | H | $CH_2$(p-MeO)Ph |
| 56 | B | H | NH | H | |
| 57 | B | 4'-Me | NH | H | |
| 58 | B | H | NH | H | |

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The following defined terms are used throughout this specification:

"Me" refers to methyl.

"Et" refers to ethyl.

"tBu" refers to t-butyl.

"iPr" refers to i-propyl.

"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R"", where R"" is aryl, C(CN)=C-aryl, $CH_2CN$, alkyaryl, sulfonamide, NH-alkyl, NH-alkylaryl, or NH-aryl.

Also, alternatively the substituent on the aniline moiety is referred to as an o, m or p substituent or a 2, 3 or 4 substituent, respectively. (Obviously, the 5 substituent is also a m substituent and the 6 substituent is an o substituent.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

Biological data for the compounds of the present invention was generated by use of the following assays.

VEGF Stimulated Ca$^{++}$ Signal in vitro

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 96-well fibronectin coated black-walled plates overnight @ 37° C./5% $CO_2$. Cells were loaded with calcium indicator Fluo-4 for 45 minutes at 37° C. Cells were washed 4 times (Original Cell Wash, Labsystems) to remove extracellular dye. Test compounds were reconstituted in 100% DMSO and added to the cells to give a final DMSO concentration of 0.1%. For screening, cells were pre-incubated with test agents for 30 minutes, at a single concentration (10 µM) or at concentrations ranging from 0.01 to 10.0 µM followed by VEGF stimulation (5 ng/mL). Changes in fluorescence at 516 nm were measured simultaneously in all 96 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

Protocol for KDR Assay:

The cytoplasmic domain of the human VEGF receptor (VEGFR-2) was expressed as a Histidine-tagged fusion protein following infection of insect cells using an engineered baculovirus. His-VEGFR-2 was purified to homogeneity, as determined by SDS-PAGE, using nickel resin chromatography. Kinase assays were performed in 96 well microtiter plates that were coated overnight with 30 µg of poly-Glu-Tyr (4:1) in 10 mM Phosphate Buffered Saline (PBS), pH 7.2-7.4. The plates were incubated with 1% BSA and then washed four times with PBS prior to starting the reaction. Reactions were carried out in 120 µL reaction volumes containing 3.6 µM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 0.5 ng of purified protein. Following a ten minute incubation at 25° C., the reactions were washed four times with PBS containing 0.05% Tween-20. 100 µl of a monoclonal anti-phosphotyrosine antibody-peroxidase conjugate was diluted 1:10000 in PBS-Tween-20 and added to the wells for 30 minutes. Following four washes with PBS-Tween-20, 100 µl of 0-Phenylenediamine Dihydrochloride in Phosphate-citrate buffer, containing urea hydrogen peroxide, was added to the wells for 7 minutes as a colorimetric substrate for the peroxidase. The reaction was terminated by the addition of 100 µl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

Miles Assay Description

VEGF-induced Dermal Extravasation in Guinea Pig (Miles Assay). Male Hartley guinea pigs (300-600 g) were anesthetized with isofluorane, sheared, and given a single oral dose of drug or the respective vehicle. Ten minutes prior to the end of drug treatment, guinea pigs were anesthetized with isofluorane, and 0.5% Evans blue dye (EBD) in PBS (13-15 mg/kg dose of EBD) was injected intravenously. After 5 minutes, triplicate intradermal injections of 100 ng rhVEGF$_{165}$ in 100 µl PBS and of 100 µl PBS alone were administered on the flank. After 20 minutes, each animal was euthanized with Pentosol, and the skin containing the intradermal injection sites was removed for image analysis.

Using an analog video camera coupled to a PC, an image of each trans-illuminated skin sample was captured, and the integrated optical density of each injection site was measured using ImagePro 4. For each skin sample, the difference between the mean optical density of the VEGF sites and mean optical density of the PBS sites is the measure of VEGF-induced EBD extravasation in that animal. These measured values were averaged per study group to determine the mean VEGF-induced EBD extravasation for each experimental condition, and the group means were then compared to assess inhibition of VEGF-induced EBD extravasation in the drug-treated groups relative to the vehicle-treated controls.

The results of said assays are set forth in Tables 2 and 3, below, wherein NT means not tested.

TABLE 2

| Example # | VEGF Stimulated Ca$^{++}$ signal assay % inhibition @ 10 µM | VEGF Stimulated Ca$^{++}$ signal assay mean IC$_{50}$(µM) | KDR Assay mean IC$_{50}$(µM) |
|---|---|---|---|
| 1 | 92.8 | 3 | NT |
| 2 | 90.5 | 1.33 | 0.58 |
| 3 | 74 | 2.44 | 0.84 |
| 4 | 92.6 | 0.70 | 0.85 |
| 5 | 98 | 0.5 | 0.18 |
| 6 | 97.64 | 1.07 | 0.50 |
| 7 | 98.27 | 0.92 | 0.54 |
| 8 | 64.50 | 3.17 | 0.97 |
| 9 | 90 | 6.14 | 1.13 |
| 10 | 76 | 3.23 | 1.03 |
| 11 | 23.42 | NT | NT |
| 12 | −12.89 | NT | 10 |
| 13 | −19.05 | NT | 10 |
| 14 | 27.45 | NT | NT |
| 15 | 6.16 | NT | NT |
| 16 | −1.47 | NT | NT |
| 17 | 27.24 | NT | NT |
| 18 | 14.13 | NT | NT |
| 19 | −0.89 | NT | NT |
| 20 | 35.81 | NT | NT |

TABLE 2-continued

| Example # | VEGF Stimulated Ca$^{++}$ signal assay % inhibition @ 10 μM | VEGF Stimulated Ca$^{++}$ signal assay mean IC$_{50}$(μM) | KDR Assay mean IC$_{50}$(μM) |
|---|---|---|---|
| 21 | 32.15 | NT | NT |
| 22 | 98.28 | 6.09 | 5.78 |
| 23 | 94.71 | 0.90 | 0.37 |
| 24 | 56.93 | 10 | 10 |
| 25 | 15.10 | NT | 10 |
| 26 | 97.06 | 0.52 | 0.33 |
| 27 | 98.62 | 1.05 | 0.53 |
| 28 | 43.88 | NT | 15.70 |
| 29 | 99.12 | 0.58 | 0.26 |
| 30 | 12.35 | NT | NT |
| 31 | −12.92 | NT | 10 |
| 32 | 46.08 | NT | 9.54 |
| 33 | 92.88 | 4.40 | 1.43 |
| 34 | 58.84 | 7.64 | 10 |
| 35 | 93.02 | 3.06 | 3.49 |
| 36 | 69.33 | 5.9 | 10 |
| 37 | 13.61 | NT | 12.68 |
| 38 | 70.04 | 6.75 | 9.90 |
| 39 | −12.56 | NT | 10 |
| 40 | −0.03 | NT | 10 |
| 41 | 96.50 | 10.0 | 0.78 |
| 42 | 0.30 | NT | 1.91 |
| 43 | 62.42 | 7.56 | 2.32 |
| 44 | 97 | 2.55 | 0.65 |
| 45 | 84.88 | 2.55 | 0.98 |
| 46 | 42.41 | NT | 11.59 |
| 47 | 79.67 | 5.92 | 2.51 |
| 48 | NT | 0.96 | 1.39 |
| 49 | NT | 0.28 | 0.57 |
| 50 | NT | 0.59 | 0.98 |
| 51 | NT | 2.32 | 1.21 |
| 52 | NT | 3.40 | 82.30 |
| 53 | NT | 1.38 | 2.22 |

As can be seen in Table 2, above, the compounds of Examples 1-10, 22, 23, 26, 27, 29, 33, 35, 41, 44, 45, 47-50 are preferred as they show either % inhibition of VEGF>79% or VEGF IC$_{50}$≦1.0 μM in either cell or kinase assay.

As also can be seen in Table 2, above, the compounds of Examples 4-7, 23, 26, 27, 29, 49 and 50 are more preferred as they show VEGF IC$_{50}$≦1.0 μM in both cell and kinase assays.

Finally, as shown in Table 3, the compounds of Examples 6 and 26 are most preferred in that they show significant in-vivo activity and therefore would be effective in oral administration.

TABLE 3

| Example # | Miles Assay dose (mg/kg) | Miles Assay vehicle | Miles Assay % inhibition |
|---|---|---|---|
| 6 | 75 | PEG400 | 83 |
| 26 | 75 | PEG400 | 100 |

The invention is further illustrated by the following non-limiting examples wherein, the starting aminopyrazoles were represented by the commercial supplier or by the accepted reaction mechanism of their formation as either 5-substituted-1H-pyrazol-3-ylamine, also know as 5-amino-3-substituted-pyrazole, or as 5-substituted-2H-pyrazol-3-ylamine, also known as 3-amino-5-substituted-pyrazole. Identification of the specifically claimed compounds as either the 4'-methyl, or 5'-fluoro, or 5'-chloro, or 6'-fluoro-substituted-3-[(5-substituted-H-pyrazol-3-ylamino)-methylene]-1,3-dihydro-indol-2-one or the 4'-methyl, or 5'-fluoro, or 5'-chloro, or 6'-fluoro-substituted-3-[(5-substituted-2H-pyrazol-3-ylamino)-methylene]-1,3-dihydro-indol-2-one is dependant on the apparent tautomeric form of the starting substituted-aminopyrazole. Specifically, if 5-substituted-1H-pyrazol-3-ylamine is used the corresponding product is represented as the 4'-methyl, or 5'-fluoro, or 5'-chloro, or 6'-fluoro substituted 3-[(5-substituted-H-pyrazol-3-ylamino)-methylene]-1,3-dihydro-indol-2-one, and conversely if or 5-substituted-2H-pyrazol-3-ylamine is used the corresponding product is represented as the 4'-methyl, or 5'-fluoro, or 5'-chloro, or 6'-fluoro substituted 3-[(5-substitute-2H-pyrazol-3-ylamino)-methylene]-1,3-dihydro-indol-2-one. Additionally, it is know to those skilled in the art that these two tautomeric forms of the pyrazole ring are prone to interconversion and therefore may be considered to be equivalent. Therefore it should be noted that the exact tautomeric identity of the pyrazole ring of the 4',5',6'-substituted-3-[(substituted-pyrazolylamino)-methylene]-1,3-dihydro-indol-2-ones claimed or the substituted-aminopyrazoles prepared within this document may be exactly as represented, the alternate tautomeric form of what is represented or some equilibrium mixture of the two forms.

EXAMPLE 1

3-[(1-H-Pyrazol-3 ylamino)methylene]-1,3-dihydro-indol-2-one 2.42 mL of ethylformate are combined with 1.33 gms of 1,3 dihydro-indol-2-one in a solution of 21%, by weight, sodium formate in ethanol. The resulting solution is allowed to stand at room temperature for 30 minutes and then refluxed for 30 minutes to yield a suspension. Once at room temperature the suspension was acidified to pH 1.0 with 10% HCl$_{(aq)}$, then 5 mL of H$_2$O was added. The resulting precipitate was filtered and washed with H$_2$O (4×20 mL) to provide a mixture of E & Z 3-[(hydroxy)-methylene]-1,3-dihydro-indol-2-one as a solid.

E & Z-3-[(hydroxy)-methylene]-1,3-dihydro-indol-2-one (0.10 g) is reacted with 0.1756 gms of 3-aminopyrazole by refluxing in tetrahydrofuran (2.7 mL) for 48 hours to yield 0.11 gms of the named compound as a solid following concentration in vacuo, dilution with isopropanol and filtration.

EXAMPLE 2

3-[(5-Phenyl-H-pyrazol-3-ylamino)-methylene]-1,3-dihydro-indol-2-one

The named compound is prepared by substituting 3-amino-5-phenylpyrazole for 3-aminopyrazole in the reaction of Example 1. Specifically, E & Z-3-[(hydroxy)-methylene]-1,3-dihydro-indol-2-one (0.10 gms.) is reacted with 0.2002 gms. of 3-amino-5-phenylpyrazole by refluxing in tetrahydrofuran (2.5 mL).

The compounds of Example 3 through 58 are prepared by substituting the appropriate substituted 3-aminopyrazole, 5-aminopyrazole or aminoisoxazole for 3-aminopyrazole, or the appropriate 4'-methyl or 5'-fluoro or 5'-chloro or 6'-fluoro substituted 1,3 dihydro-indol-2-one for 1,3 dihydro-indol-2-one in the reaction of Example 1.

EXAMPLE 3

3-[(5-P-Tolyl-1H-pyrazol-3-ylamino)-methylene]-1,3-dihydro-indol-2-one

The named compound is prepared by substituting 3-amino-5-(p-tolyl)-pyrazole for 3-aminopyrazole in the reaction of Example 1. Specifically, E & Z-3-[(hydroxy)-methylene]-1, 3-dihydro-indol-2-one (0.10 gms.) is reacted with 0.1480 gms. of 3-amino-5-(p-tolyl)-pyrazole by refluxing in tetrahydrofuran (2.5 mL).

EXAMPLE 4

3-[(5-Furan-2-yl-1H-pyrazol-3-ylamino)-methylene]-1,3-dihydro-indol-2-one

The named compound is prepared by substituting 3-amino-5-(2-furyl)-pyrazole for 3-aminopyrazole in the reaction of Example 1. Specifically, E & Z-3-[(hydroxy)-methylene]-1,3-dihydro-indol-2-one (0.10 gms.) is reacted with 0.1480 gms. of 3-amino-5-(2-furyl)-pyrazole by refluxing in tetrahydrofuran (2.5 mL).

EXAMPLE 5

3-{[5-(4-Methoxy-benzyl)-1H-pyrazol-3-ylamino]-methylene}-1,3-dihydro-indol-2-one The named compound is prepared by substituting 5-(4-methoxy-benzyl)-1H-pyrazol-3-ylamine for 3-aminopyrazole in the reaction of Example 1. Specifically, E & Z-3-[(hydroxy)-methylene]-1,3-dihydro-indol-2-one (0.041 gms.) is reacted with 0.078 gms. of 5-(4-methoxy-benzyl)-1H-pyrazol-3-ylamine by refluxing in tetrahydrofuran (1.0 mL).

5-(4-Methoxy-benzyl)-1H-pyrazol-3-ylamine

The named compound is the 3-aminopyrazole used in the reaction of Example 5 and can be prepared from ethyl methoxyphenyl acetate by the following method:

Dry acetonitrile (0.738 gms.) is mixed with 24.5 mL THF under $Ar_{(g)}$ and cooled to −78° C. in a dry ice-acetone bath. Dropwise addition of 2M n-butyl lithium in cyclohexane (7.72 mL) to this mixture then affords a yellowish/orange color solution. The mixture is allowed to stir at −78° C. for an additional 1.5 h followed by dropwise addition of ethyl 4-methoxy phenyl acetate (2.5 gms.). The resulting solution is stirred at −78° C. for an additional 30 minutes and then is stirred overnight at room temperature. Subsequently, the reaction mixture is treated with dilute NaOH, to dissolve solid material that forms, and extracted twice with water. The combined aqueous layers are neutralized with a saturated aqueous $NH_4Cl$ solution and extracted twice with EtOAc. The combined organic layers are dried over anhydrous $Na_2SO_4$ and concentrated in vacuo. The crude product is recrystallized from hot i-prOH to yield the desired 4-(4-methoxy-phenyl)-3-oxo-butyronitile in 11% yield. This nitrile (0.225 gms.) is then dissolved in 5 mL anydrous EtOH, treated with anhydrous hydrazine (0.081 gms.) and heated to 65° C. The resulting reaction mixture is stirred overnight at 65° C., subsequently cooled to room temperature, and concentrated in vacuo to provide the named compound.

EXAMPLE 6

4-Methyl-3-[(1H-pyrazol-3-ylamino)-methylene]-1,3-dihydro-indol-2-one

The named compound is prepared by substituting E & Z-3-[(hydroxy)-methylene]-4-methyl-1,3-dihydro-indol-2-one for E & Z-3-[(hydroxy)-methylene]-1,3-dihydro-indol-2-one in the reaction of Example 1. Specifically, E & Z-3-[(hydroxy)-methylene]-4-methyl-1,3-dihydro-indol-2-one (0.110 gms.) is reacted with 0.18 mL of 3-aminopyrazole by refluxing in tetrahydrofuran (2.5 mL).

EXAMPLE 7

3-[(5-Furan-2-yl-1H-pyrazol-3-ylamino)-methylene]-4-methyl-1,3-dihydro-indol-2-one The named compound is prepared by substituting E & Z-3-[(hydroxy)-methylene]-4-methyl-1,3-dihydro-indol-2-one for E & Z-3-[(hydroxy)-methylene]-1,3-dihydro-indol-2-one and substituting 3-amino-5-(2-furyl)-pyrazole for 3-aminopyrazole in the reaction of Example 1. Specifically, E & Z-3-[(hydroxy)-methylene]-4-methyl-1,3-dihydro-indol-2-one (0.110 gms.) is reacted with 0.2065 gms. of 3-amino-5-(2-furyl)-pyrazole by refluxing in tetrahydrofuran (2.5 mL).

EXAMPLE 8

4-Methyl-3-[(5-phenyl-1H-pyrazol-3-ylamino)-methylene]-1,3-dihydro-indol-2-one

The named compound is prepared by substituting E & Z-3-[(hydroxy)-methylene]-4-methyl-1,3-dihydro-indol-2-one for E & Z-3-[(hydroxy)-methylene]-1,3-dihydro-indol-2-one and substituting 3-amino-5-phenylpyrazole for 3-aminopyrazole in the reaction of Example 1. Specifically, E & Z-3-[(hydroxy)-methylene]-4-methyl-1,3-dihydro-indol-2-one (0.110 gms.) is reacted with 0.2398 gms. 3-amino-5-phenylpyrazole by refluxing in tetrahydrofuran (2.5 mL).

EXAMPLE 9

5-Chloro-3-[(1H-pyrazol-3-ylamino)-methylene]-1,3-dihydro-indol-2-one

The named compound is prepared by substituting E & Z-3-[(hydroxy)-methylene]-5-chloro-1,3-dihydro-indol-2-one for E & Z-3-[(hydroxy)-methylene]-1,3-dihydro-indol-2-one in the reaction of Example 1. Specifically, E & Z-3-[(hydroxy)-methylene]-5-chloro-1,3-dihydro-indol-2-one is reacted with 0.300 gms 3-aminopyrazole by refluxing in tetrahydrofuran.

EXAMPLE 10

3-[(5-Furan-2-yl-1H-pyrazol-3-ylamino)-methylene]-5-chloro-1,3-dihydro-indol-2-one The named compound is prepared by substituting E & Z-3-[(hydroxy)-methylene]-5-chloro-1,3-dihydro-indol-2-one for E & Z-3-[(hydroxy)-methylene]-1,3-dihydro-indol-2-one and substituting 3-amino-5-(2-furyl)-pyrazole for 3-aminopyrazole in the reaction of Example 1. Specifically, E & Z-3-[(hydroxy)-methylene]-5-chloro-1,3-dihydro-indol-2-one is reacted with 0.280 gms. 3-amino-5-(2-furyl)-pyrazole by refluxing in tetrahydrofuran.

EXAMPLE 11

3-[(4-Bromo-5-phenyl-1H-pyrazol-3-ylamino)-methylene]-1,3-dihydro-indol-2-one

The named compound is prepared by substituting 4-bromo-5-phenyl-1H-pyrazol-3-ylamine for 3-aminopyrazole in the reaction of Example 1. Specifically, E & Z-3-

[(hydroxy)-methylene]-1,3-dihydro-indol-2-one (0.1489 gms.) is reacted with 0.4557 gms. of 4-bromo-5-phenyl-1H-pyrazol-3-ylamine by refluxing in tetrahydrofuran (3.0 mL).

EXAMPLE 12

3-[(4-Bromo-5-phenyl-1H-pyrazol-3-ylamino)-methylene]-4-methyl-1,3-dihydro-indol-2-one The named compound is prepared by substituting E & Z-3-[(hydroxy)-methylene]-4-methyl-1,3-dihydro-indol-2-one for E & Z-3-[(hydroxy)-methylene]-1,3-dihydro-indol-2-one and 4-bromo-5-phenyl-1H-pyrazol-3-ylamine for 3-aminopyrazole in the reaction of Example 1. Specifically, E & Z-3-[(hydroxy)-methylene]-4-methyl-1,3-dihydro-indol-2-one (0.1622 gms.) is reacted with 0.4530 gms. of 4-bromo-5-phenyl-1H-pyrazol-3-ylamine by refluxing in tetrahydrofuran (3.0 mL).

EXAMPLE 13

3-[(4-Bromo-5-phenyl-1H-pyrazol-3-ylamino)-methylene]-5-chloro-1,3-dihydro-indol-2-one The named compound is prepared by substituting E & Z-3-[(hydroxy)-methylene]-5-chloro-1,3-dihydro-indol-2-one for E & Z-3-[(hydroxy)-methylene]-1,3-dihydro-indol-2-one and 4-bromo-5-phenyl-1H-pyrazol-3-ylamine for 3-aminopyrazole in the reaction of Example 1. Specifically, E & Z-3-[(hydroxy)-methylene]-5-chloro-1,3-dihydro-indol-2-one (0.1820 gms.) is reacted with 0.4511 gms. of 4-bromo-5-phenyl-1H-pyrazol-3-ylamine by refluxing in tetrahydrofuran (3.0 mL).

EXAMPLE 14

5-Chloro-3-[(5-phenyl-1H-pyrazol-3-ylamino)-methylene]-1,3-dihydro-indol-2-one

The named compound is prepared by substituting E & Z-3-[(hydroxy)-methylene]-5-chloro-1,3-dihydro-indol-2-one for E & Z-3-[(hydroxy)-methylene]-1,3-dihydro-indol-2-one and 3-amino-5-phenylpyrazole for 3-aminopyrazole in the reaction of Example 1. Specifically, E & Z-3-[(hydroxy)-methylene]-5-chloro-1,3-dihydro-indol-2-one (0.100 gms.) is reacted with 0.1668 gms. of 3-amino-5-phenylpyrazole by refluxing in tetrahydrofuran (2.5 mL).

EXAMPLE 15

3-[(4-Fluoro-1H-indazol-3-ylamino)-methylene]-1,3-dihydro-indol-2-one

The named compound is prepared by substituting 4-fluoro-1H-indazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2186 gms. of 4-fluoro-1H-indazol-3-ylamine by refluxing in tetrahydrofuran (2.5 mL).

EXAMPLE 16

3-{[4-(3,4-Dimethoxy-phenyl)-5-methyl-2H-pyrazol-3-ylamino]-methylene}-1,3-dihydro-indol-2-one The named compound is prepared by substituting 4-(3,4-dimethoxy-phenyl)-5-methyl-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2085 gms. of 4-(3,4-dimethoxy-phenyl)-5-methyl-2H-pyrazol-3-ylamine by refluxing in tetrahydrofuran (2.5 mL).

EXAMPLE 17

3-[(2-Oxo-1,2-dihydro-indol-3-ylidenemethyl)-amino]-1H-pyrazole-4-carboxylic acid ethyl ester The named compound is prepared by substituting 3-amino-1H-pyrazole-4-carboxylic acid ethyl ester for 3-aminopyrazole in the reaction of Example 1. Specifically, E & Z-3-[(hydroxy)-methylene]-1,3-dihydro-indol-2-one (0.100 gms.) is reacted with 0.2001 gms. of 3-amino-1H-pyrazole-4-carboxylic acid ethyl ester by refluxing in tetrahydrofuran (2.5 mL).

EXAMPLE 18

5-Methylsulfanyl-3-[(2-oxo-1,2-dihydro-indol-3-ylidenemethyl)-amino]-1H-pyrazole-4-carbonitrile The named compound is prepared by substituting 3-amino-5-methylsulfanyl-1H-pyrazole-4-carbonitrile for 3-aminopyrazole in the reaction of Example 1. Specifically, E & Z-3-[(hydroxy)-methylene]-1,3-dihydro-indol-2-one (0.100 gms.) is reacted with 0.2003 gms. of 3-amino-5-methylsulfanyl-1H-pyrazole-4-carbonitrile by refluxing in tetrahydrofuran (2.5 mL).

EXAMPLE 19

3-[(2-Oxo-1,2-dihydro-indol-3-ylidenemethyl)-amino]-1H-pyrazole-4-carboxylic acid The named compound is prepared by substituting 3-amino-1H-pyrazole-4-carboxylic acid for 3-aminopyrazole in the reaction of Example 1. Specifically, E & Z-3-[(hydroxy)-methylene]-1,3-dihydro-indol-2-one (0.100 gms.) is reacted with 0.1601 gms. of 3-amino-1H-pyrazole-4-carboxylic acid by refluxing in tetrahydrofuran (2.5 mL).

EXAMPLE 20

3-[(2-Oxo-1,2-dihydro-indol-3-ylidenemethyl)-amino]-1H-pyrazole-4-carbonitrile

The named compound is prepared by substituting 3-amino-1H-pyrazole-4-carbonitrile for 3-aminopyrazole in the reaction of Example 1. Specifically, E & Z-3-[(hydroxy)-methylene]-1,3-dihydro-indol-2-one (0.100 gms.) is reacted with 0.1511 gms. of 3-amino-1H-pyrazole-4-carbonitrile by refluxing in tetrahydrofuran (2.5 mL).

EXAMPLE 21

3-[(4-Bromo-1H-pyrazol-3-ylamino)-methylene]-1,3-dihydro-indol-2-one

The named compound is prepared by substituting 4-bromo-1H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2141 gms. of 4-bromo-1H-pyrazol-3-ylamine by refluxing in tetrahydrofuran (2.5 mL).

EXAMPLE 22

3-[(5-tert-Butyl-1H-pyrazol-3-ylamino)-methylene]-1,3-dihydro-indol-2-one

The named compound is prepared by substituting 5-tert-butyl-1H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.1920 gms. of 5-tert-butyl-1H-pyrazol-3-ylamine by refluxing in tetrahydrofuran (2.5 mL).

EXAMPLE 23

3-[(5-Methyl-1H-pyrazol-3-ylamino)-methylene]-1,3-dihydro-indol-2-one

The named compound is prepared by substituting 5-methyl-1H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.1345 gms. of 5-methyl-1H-pyrazol-3-ylamine by refluxing in tetrahydrofuran (2.5 mL).

EXAMPLE 24

4-{5-[(2-Oxo-1,2-dihydro-indol-3-ylidenemethyl)-amino]-2H-pyrazol-3-yl}-benzoic acid methyl ester The named compound is prepared by substituting 4-(5-amino-2H-pyrazol-3-yl)-benzoic acid methyl ester for 3-aminopyrazole in the reaction of Example 1. Specifically, E & Z-3-[(hydroxy)-methylene]-1,3-dihydro-indol-2-one (0.100 gms.) is reacted with 0.2847 gms. of 4-(5-amino-2H-pyrazol-3-yl)-benzoic acid methyl ester by refluxing in tetrahydrofuran (2.5 mL).

4-(5-Amino-2H-pyrazol-3-yl)-benzoic acid methyl ester

The named compound is the 3-aminopyrazole used in the reaction of Example 23 and can be prepared from commercially available 4-(2-cyano-acetyl)-benzoic acid methyl ester by the following method:

4-(2-Cyano-acetyl)-benzoic acid methyl ester (1.0 gm.) is dissolved in 9.29 mL anydrous EtOH, treated with anhydrous hydrazine (0.37 mL) and heated to reflux. The resulting reaction mixture is refluxed for 24 h, subsequently cooled to room temperature, and concentrated in vacuo to provide the named compound in the amount of 0.45 gms.

EXAMPLE 25

3-[(4,6-Dimethyl-1H-pyrazolo[3,4-b]pyridin-3-ylamino)-methylene]-1,3-dihydro-indol-2-one The named compound is prepared by substituting 4,6-dimethyl-1H-pyrazolo[3,4-b]pyridin-3-ylamine for 3-aminopyrazole in the reaction of Example 1. Specifically, E & Z-3-[(hydroxy)-methylene]-1,3-dihydro-indol-2-one (0.100 gms.) is reacted with 0.2118 gms. of 4,6-dimethyl-1H-pyrazolo[3,4-b]pyridin-3-ylamine by refluxing in tetrahydrofuran (2.5 mL).

EXAMPLE 26

5-Fluoro-3-[(5-methyl-1H-pyrazol-3-ylamino)-methylene]-1,3-dihydro-indol-2-one The named compound is prepared by substituting E & Z-3-[(hydroxy)-methylene]-5-fluoro-1,3-dihydro-indol-2-one for E & Z-3-[(hydroxy)-methylene]-1,3-dihydro-indol-2-one and 5-methyl-1H-pyrazol-3-ylamine for 3-aminopyrazole in the reaction of Example 1. Specifically, E & Z-3-[(hydroxy)-methylene]-5-fluoro-1,3-dihydro-indol-2-one (0.050 gms.) is reacted with 0.055 gms. of 5-methyl-1H-pyrazol-3-ylamine by refluxing in tetrahydrofuran (1.5 mL).

EXAMPLE 27

5-Fluoro-3-[(5-furan-2-yl-1H-pyrazol-3-ylamino)-methylene]-1,3-dihydro-indol-2-one The named compound is prepared by substituting E & Z-3-[(hydroxy)-methylene]-5-fluoro-1,3-dihydro-indol-2-one for E & Z-3-[(hydroxy)-methylene]-1,3-dihydro-indol-2-one and 3-amino-5-(2-furyl)-pyrazole for 3-aminopyrazole in the reaction of Example 1. Specifically, E & Z-3-[(hydroxy)-methylene]-5-fluoro-1,3-dihydro-indol-2-one (0.050 gms.) is reacted with 0.085 gms. of 3-amino-5-(2-furyl)-pyrazole by refluxing in tetrahydrofuran (1.5 mL).

EXAMPLE 28

3-{[5-(5-tert-Butyl-2-methyl-furan-3-yl)-2H-pyrazol-3-ylamino]-methylene}-5-fluoro-1,3-dihydro-indol-2-one The named compound is prepared by substituting E & Z-3-[(hydroxy)-methylene]-5-fluoro-1,3-dihydro-indol-2-one for E & Z-3-[(hydroxy)-methylene]-1,3-dihydro-indol-2-one and 5-(5-tert-butyl-2-methyl-furan-3-yl)-2H-pyrazol-3-ylamine for 3-aminopyrazole in the reaction of Example 1. Specifically, E & Z-3-[(hydroxy)-methylene]-5-fluoro-1,3-dihydro-indol-2-one (0.050 gms.) is reacted with 0.123 gms. of 3-{[5-(5-tert-butyl-2-methyl-furan-3-yl)-2H-pyrazol-3-ylamino]-methylene}-5-fluoro-1,3-dihydro-indol-2-one by refluxing in tetrahydrofuran (1.5 mL).

EXAMPLE 29

3-{[5-(5-tert-Butyl-2-methyl-furan-3-yl)-2H-pyrazol-3-ylamino]-methylene}-1,3-dihydro-indol-2-one The named compound is prepared by substituting 5-(5-tert-butyl-2-methyl-furan-3-yl)-1H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2987 gms. of 5-(5-tert-butyl-2-methyl-furan-3-yl)-2H-pyrazol-3-ylamine by refluxing in tetrahydrofuran (2.5 mL).

EXAMPLE 30

3-{[5-(4-Methoxy-phenyl)-2H-pyrazol-3-ylamino]-methylene}-1,3-dihydro-indol-2-one The named compound is prepared by substituting 5-(4-methoxy-phenyl)-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2392 gms. of 5-(4-methoxy-phenyl)-2H-pyrazol-3-ylamine by refluxing in tetrahydrofuran (2.5 mL).

5-(4-Methoxy-phenyl)-2H-pyrazol-3-ylamine

The named compound is the 3-aminopyrazole used in the reaction of Example 30 and can be prepared from commercially available 3-(4-methoxy-phenyl)-3-oxo-propionitrile by the following method:

3-(4-Methoxy-phenyl)-3-oxo-propionitrile (1.0 gm.) is dissolved in 10.8 mL anydrous EtOH, treated with anhydrous hydrazine (0.43 mL) and heated to reflux. The resulting reaction mixture is refluxed overnight, subsequently cooled to room temperature, and concentrated in vacuo. The crude residue is then triturated with diethyl ether and ethyl acetate to provide the named compound in the amount of 0.86 gms.

EXAMPLE 31

3-{[5-(3,5-Bis-benzyloxy-phenyl)-2H-pyrazol-3-ylamino]-methylene}-1,3-dihydro-indol-2-one The named compound is prepared by substituting 5-(3,5-bis-benzyloxy-phenyl)-2H-pyrazol-3-ylamine hydrochloride for 3-aminopyrazole in the reaction of Example 1. Specifically, E & Z-3-[(hydroxy)-methylene]-1,3-dihydro-indol-2-one (0.030 gms.) is reacted with 0.114 gms. of 5-(3,5-bis-benzyloxy-phenyl)-2H-pyrazol-3-ylamine hydrochloride by refluxing in tetrahydrofuran (2.0 mL).

5-(3,5-Bis-benzyloxy-phenyl)-2H-pyrazol-3-ylamine hydrochloride

The named compound is the 3-aminopyrazole used in the reaction of Example 31 and can be prepared from (3,5-bis-benzyloxy-phenyl)-acetic acid ethyl ester by the following method:

Under $Ar_{(g)}$, a solution of anhydrous acetonitrile (0.83 mL) in 25 mL anhydrous THF is cooled to −78° C. in a dry ice-acetone bath and then treated in dropwise fashion with 6.32 mL of a 2.5 M n-butyl lithium in hexanes. The reaction mixture is maintained at −78° C. for an additional 1 h and subsequently treated in dropwise fashion with a solution of 5 gms. of (3,5-bis-benzyloxy-phenyl)-acetic acid ethyl ester in 25 mL of anhydrous THF. The resulting solution is then stirred overnight at room temperature. Subsequently, the reaction mixture is diluted with ethyl acetate and then extracted with 10% $NaOH_{(aq)}$. The aqueous layer is acidified (pH 6-7) with a 1 M $HCl_{(aq)}$ solution affording a white precipitate. The precipitate is filtered and washed with water. The filtrate was then extracted ethyl acetate. The organic layer is concentrated in vacuo. The organic extraction yielded very little of the 3-(3,5-bis-benzyloxy-phenyl)-3-oxo-propionitrile, however, the precipitate isolated from the acidification of the original aqueous layer is indeed the desired 3-(3,5-bis-benzyloxy-phenyl)-3-oxo-propionitrile. Upon drying the precipitate in vacuo the desired 3-(3,5-bis-benzyloxy-phenyl)-3-oxo-propionitrile is isolated as a brownish white solid in the amount of 3.43 gms. (67% yield).

3-(3,5-Bis-benzyloxy-phenyl)-3-oxo-propionitrile (3.4157 gms.) is then suspended in 50 mL of anhydrous EtOH. This suspension is treated with 0.6 mL of anhydrous hydrazine and subsequently heated to refluxing temperature for 2 h. The reaction mixture is concentrated in vacuo. The residue is then treated with an icy slurry of aqueous HCl to precipitate out the 5-(3,5-bis-benzyloxy-phenyl)-2H-pyrazol-3-ylamine hydrochloride as a white solid in the amount of 3.45 gms. (88% yield).

EXAMPLE 32

3-{[5-(3,5-Dimethyl-phenyl)-2H-pyrazol-3-ylamino]-methylene}-1,3-dihydro-indol-2-one The named compound is prepared by substituting 5-(3,5-dimethyl-phenyl)-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2381 gms. 5-(3,5-dimethyl-phenyl)-2H-pyrazol-3-ylamine by refluxing in tetrahydrofuran (2.0 mL) over the weekend.

5-(3,5-Dimethyl-phenyl)-2H-pyrazol-3-ylamine

The named compound is the 3-aminopyrazole used in the reaction of Example 32 and can be prepared from 3,5-dimethyl-benzoic acid ethyl ester by the following method:

Under $Ar_{(g)}$, a solution of anhydrous acetonitrile (1.6 mL) in 35 mL anhydrous THF is cooled to −78° C. in a dry ice-acetone bath and then slowly treated with 12 mL of a 2.5 M n-butyl lithium in hexanes. The reaction mixture is maintained at −78° C. for an additional 45 min. and then slowly treated with a solution of 5 gms. of 3,5-dimethyl-benzoic acid ethyl ester in 5 mL of anhydrous THF. The resulting solution is then stirred overnight at room temperature. Subsequently, the reaction mixture is treated with 10% $NaOH_{(aq)}$ to dissolve solids, and then is extracted with ethyl acetate. The aqueous layer is acidified (pH 6) with $HCl_{(aq)}$ affording a white precipitate which subsequently is filtered The organic layer is concentrated in vacuo and the residue is triturated with isopropanol resulting in the formation of additional white precipitate. The combined precipitates provide the desired 3-(3,5-dimethyl-phenyl)-3-oxo-propionitrile in the amount of 2.0175 gms.

3-(3,5-Dimethyl-phenyl)-3-oxo-propionitrile (2.0175 gms.) is then suspended in 55 mL of anhydrous EtOH. This suspension is treated with 0.73 mL of anhydrous hydrazine and subsequently heated to refluxing temperature for 1 day. The reaction mixture is concentrated in vacuo. The residue is then triturated with isopropanol to precipitate out the 5-(3,5-dimethyl-phenyl)-2H-pyrazol-3-ylamine as a white solid.

EXAMPLE 33

3-{[5-(3-Methoxy-phenyl)-2H-pyrazol-3-ylamino]-methylene}-1,3-dihydro-indol-2-one The named compound is prepared by substituting 5-(3-methoxy-phenyl)-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2367 gms. 5-(3-methoxy-phenyl)-2H-pyrazol-3-ylamine by refluxing in tetrahydrofuran (2.0 mL) over the weekend.

5-(3-Methoxy-phenyl)-2H-pyrazol-3-ylamine

The named compound is the 3-aminopyrazole used in the reaction of Example 33 and can be prepared from 3-methoxy-benzoic acid ethyl ester by the following method:

Under $Ar_{(g)}$, a solution of anhydrous acetonitrile (1.6 mL) in 35 mL anhydrous THF is cooled to −78° C. in a dry ice-acetone bath and then slowly treated with 12 mL of a 2.5 M n-butyl lithium in hexanes. The reaction mixture is maintained at −78° C. for an additional 45 min. and then slowly treated with a solution of 5gms. of 3-methoxy-benzoic acid ethyl ester in 5 mL of anhydrous THF. The resulting solution is then stirred overnight at room temperature. Subsequently, the reaction mixture is treated with 10% NaOH$_{(aq)}$ to dissolve solids, and then is extracted with ethyl acetate. The aqueous layer is acidified (pH 6) with HCl$_{(aq)}$ affording a white precipitate which subsequently is filtered The organic layer is concentrated in vacuo and the residue is triturated with isopropanol resulting in the formation of additional white precipitate. The combined precipitates provide the desired 3-(3-methoxy-phenyl)-3-oxo-propionitrile in the amount of 2.0202 gms.

3-(3-Methoxy-phenyl)-3-oxo-propionitrile (2.0202 gms.) is then suspended in 55 mL of anhydrous EtOH. This suspension is treated with 0.73 mL of anhydrous hydrazine and subsequently heated to refluxing temperature for 1 day. The reaction mixture is concentrated in vacuo. The residue is then triturated with isopropanol to precipitate out the 5-(3-methoxy-phenyl)-2H-pyrazol-3-ylamine as a white solid.

EXAMPLE 34

3-{[5-(2,4-Dimethyl-phenyl)-2H-pyrazol-3-ylamino]-methylene}-1,3-dihydro-indol-2-one The named compound is prepared by substituting 5-(2,4-dimethyl-phenyl)-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.250 gms. 5-(2,4-dimethyl-phenyl)-2H-pyrazol-3-ylamine by refluxing in tetrahydrofuran (2.0 mL) over the weekend.

5-(2,4-Dimethyl-phenyl)-2H-pyrazol-3-ylamine

The named compound is the 3-aminopyrazole used in the reaction of Example 34 and can be prepared from 2,4-dimethyl-benzoic acid ethyl ester by the following method:

Under Ar$_{(g)}$, a solution of anhydrous acetonitrile (1.6 mL) in 35 mL anhydrous THF is cooled to −78° C. in a dry ice-acetone bath and then slowly treated with 12 mL of a 2.5 M n-butyl lithium in hexanes. The reaction mixture is maintained at −78° C. for an additional 45 min. and then slowly treated with a solution of 5 gms. of 2,4-dimethyl-benzoic acid ethyl ester in 5 mL of anhydrous THF. The resulting solution is then stirred overnight at room temperature. Subsequently, the reaction mixture is treated with 10% NaOH$_{(aq)}$ to dissolve solids and then extracted with ethyl acetate. The aqueous layer is acidified (pH 6) with HCl$_{(aq)}$ affording a white precipitate which subsequently is filtered The organic layer is concentrated in vacuo and the residue is triturated with isopropanol resulting in the formation of additional white precipitate. The combined precipitates provide the desired 3-(2,4-dimethyl-phenyl)-3-oxo-propionitrile in the amount of 2.0011 gms.

3-(2,4-Dimethyl-phenyl)-3-oxo-propionitrile (2.0011 gms.) is then suspended in 55 mL of anhydrous EtOH. This suspension is treated with 0.73 mL of anhydrous hydrazine, and subsequently is heated to refluxing temperature for 1 day. The reaction mixture is concentrated in vacuo. The residue is then triturated with isopropanol to precipitate out the 5-(2,4-dimethyl-phenyl)-2H-pyrazol-3-ylamine as a white solid.

EXAMPLE 35

3-{[5-(4-Dimethylamino-phenyl)-2H-pyrazol-3-ylamino]-methylene}-1,3-dihydro-indol-2-one The named compound is prepared by substituting 5-(4-dimethylamino-phenyl)-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2543 gms. 5-(4-dimethylamino-phenyl)-2H-pyrazol-3-ylamine by refluxing in tetrahydrofuran (2.0 mL) overnight.

5-(4-Dimethylamino-phenyl)-2H-pyrazol-3-ylamine

The named compound is the 3-aminopyrazole used in the reaction of Example 35 and can be prepared from 4-dimethylamino-benzoic acid ethyl ester by the following method:

Under Ar$_{(g)}$, a solution of anhydrous acetonitrile (1.9 mL) in 25 mL anhydrous THF is cooled to −78° C. in a dry ice-acetone bath and then treated in dropwise fashion with 14.3 mL of a 2.5 M n-butyl lithium in hexanes. The reaction mixture is maintained at −78° C. for an additional 1 h and subsequently treated in dropwise fashion with a solution of 5 gms. of 4-dimethylamino-benzoic acid ethyl ester in 25 mL of anhydrous THF. The resulting solution is then stirred overnight at room temperature. Subsequently, the reaction mixture is diluted with ethyl acetate and then extracted with 10% NaOH$_{(aq)}$. The aqueous layer is acidified (pH 6-7) with a 1 M HCl$_{(aq)}$ solution affording a white precipitate. The precipitate is filtered and washed with water. The filtrate is then extracted ethyl acetate. The organic layer is concentrated in vacuo. The organic extraction yields very little of the expected 3-(4-dimethylamino-phenyl)-3-oxo-propionitrile, however, the precipitate isolated from the acidification of the original aqueous layer is indeed the desired 3-(4-dimethylamino-phenyl)-3-oxo-propionitrile. Upon drying the precipitate in vacuo, the desired 3-(4-dimethylamino-phenyl)-3-oxo-propionitrile is isolated as a light brown solid in the amount of 3.295 gms. (68% yield).

3-(4-Dimethylamino-phenyl)-3-oxo-propionitrile (3.262 gms.) is then suspended in 100 mL of anhydrous EtOH. This suspension is treated with 1.09 mL of anhydrous hydrazine, and subsequently is heated to refluxing temperature for 2 h. The reaction mixture is cooled to room temperature and stored in a −20° C. freezer overnight to yield a white crystalline precipitate. This precipitate is filtered and the filtrate is concentrated in vacuo. The residue from the evaporation is triturated with ethyl acetate to give additional precipitate. The combined precipitates are again triturated with ethyl acetate for 45 min. due to the presence of starting material in the initial precipitate. The solid material is collected by filtration providing the 5-(4-dimethylamino-phenyl)-2H-pyrazol-3-ylamine in the amount of 0.86 gms. (37% yield).

EXAMPLE 36

3-{[5-(2,3,5-Trimethyl-benzyl)-2H-pyrazol-3-ylamino]-methylene}-1,3-dihydro-indol-2-one The named compound is prepared by substituting 5-(2,4,6-trimethyl-benzyl)-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2758 gms. 5-(2,4,6-trimethyl-benzyl)-2H-pyrazol-3-ylamine by refluxing in tetrahydrofuran (2.0 mL) overnight.

5-(2,4,6-Trimethyl-benzyl)-2H-pyrazol-3-ylamine

The named compound is the 3-aminopyrazole used in the reaction of Example 36 and can be prepared from (2,4,6-trimethyl-phenyl)-acetic acid ethyl ester by the following method:

Under Ar$_{(g)}$, a solution of anhydrous acetonitrile (0.506 mL) in 25 mL anhydrous THF is cooled to −78° C. in a dry ice-acetone bath and then treated in dropwise fashion with 6.0 mL of a 1.6 M n-butyl lithium in hexanes. The reaction mixture is maintained at −78° C. for an additional 1 h and subsequently treated in dropwise fashion with a solution of 5 gms. of (2,4,6-trimethyl-phenyl)-acetic acid ethyl ester in 25 mL of anhydrous THF. The resulting solution is then stirred 5 h at room temperature. Subsequently, the reaction mixture is acidified (pH 7-8) with dropwise addition of conc. HCl and a 1 M HCl$_{(aq)}$ solution. The quenched reaction mixture is then partitioned between water and ethyl acetate. The organic layer is dried over anhydrous Na$_2$SO$_4$, filtered and concentrated in vacuo to yield the desired 3-oxo-4-(2,4,6-trimethyl-phenyl)-butyronitrile as a yellow-white solid in the amount of 1.41 gms. (72% yield).

3-Oxo-4-(2,4,6-trimethyl-phenyl)-butyronitrile (1.37 gms.) is then suspended in 20 mL of anhydrous EtOH. This suspension is treated with 0.428 mL of anhydrous hydrazine, and subsequently is heated to refluxing temperature overnight. The reaction mixture is cooled to room temperature and evaporated to dryness in vacuo to yield 1.73 gms. of a yellow oil. This oil is then triturated with warm ethyl acetate for 45 min. to provide a yellow-white precipitate. Collection of this precipitate by filtration provides the desired 5-(2,4,6-trimethyl-benzyl)-2H-pyrazol-3-ylamine in the amount of 0.498 gms.

EXAMPLE 37

3-{[5-(2-Methoxy-phenyl)-2H-pyrazol-3-ylamino]-methylene}-1,3-dihydro-indol-2-one The named compound is prepared by substituting 5-(2-methoxy-phenyl)-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2551 gms. 5-(2-methoxy-phenyl)-2H-pyrazol-3-ylamine by refluxing in tetrahydrofuran (2.0 mL) overnight.

5-(2-Methoxy-phenyl)-2H-pyrazol-3-ylamine

The named compound is the 3-aminopyrazole used in the reaction of Example 37 and can be prepared from 2-methoxy-benzoic acid ethyl ester by the following method:

Under Ar$_{(g)}$, a solution of anhydrous acetonitrile (1.6 mL) in 35 mL anhydrous THF is cooled to −78° C. in a dry ice-acetone bath and then slowly treated with 12 mL of a 2.5 M n-butyl lithium in hexanes. The reaction mixture is maintained at −78° C. for an additional 45 min. and then slowly treated with a solution of 5 gms. of 2-methoxy-benzoic acid ethyl ester in 5 mL of anhydrous THF. The resulting solution is then stirred overnight at room temperature. Subsequently, the reaction mixture is treated with 10% NaOH$_{(aq)}$ to dissolve solids and then extracted with ethyl acetate. The aqueous layer is acidified (pH 6) with HCl$_{(aq)}$ affording a white precipitate which subsequently is filtered The organic layer is concentrated in vacuo and the residue is triturated with isopropanol resulting in the formation of additional white precipitate. The combined precipitates provide the desired 3-(2-methoxy-phenyl)-3-oxo-propionitrile in the amount of 2.4954 gms.

3-(2-Methoxy-phenyl)-3-oxo-propionitrile (2.4954 gms.) is then suspended in 55 mL of anhydrous EtOH. This suspension is treated with 0.90 mL of anhydrous hydrazine and subsequently heated to refluxing temperature for 1 day. The reaction mixture is concentrated in vacuo. The residue is then triturated with isopropanol to precipitate out the 5-(2-methoxy-phenyl)-2H-pyrazol-3-ylamine.

EXAMPLE 38

3-{[5-(4-Ethoxy-phenyl)-2H-pyrazol-3-ylamino]-methylene}-1,3-dihydro-indol-2-one The named compound is prepared by substituting 5-(4-ethoxy-phenyl)-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2635 gms. 5-(4-ethoxy-phenyl)-2H-pyrazol-3-ylamine by refluxing in tetrahydrofuran (2.0 mL) overnight.

5-(4-Ethoxy-phenyl)-2H-pyrazol-3-ylamine

The named compound is the 3-aminopyrazole used in the reaction of Example 38 and can be prepared from 4-ethoxy-benzoic acid ethyl ester by the following method:

Under Ar$_{(g)}$, a solution of anhydrous acetonitrile (1.5 mL) in 35 mL anhydrous THF is cooled to −78° C. in a dry ice-acetone bath and then slowly treated with 11 mL of a 2.5 M n-butyl lithium in hexanes. The reaction mixture is maintained at −78° C. for an additional 45 min. and then slowly treated with a solution of 5 gms. of 4-ethoxy-benzoic acid ethyl ester in 5 mL of anhydrous THF. The resulting solution is then stirred overnight at room temperature. Subsequently, the reaction mixture is treated with 10% NaOH$_{(aq)}$ to dissolve solids and then extracted with ethyl acetate. The aqueous layer is acidified (pH 6) with HCl$_{(aq)}$ affording a white precipitate which subsequently is filtered The organic layer is concentrated in vacuo and the residue is triturated with isopropanol resulting in the formation of additional white precipitate. The combined precipitates provide the desired 3-(4-ethoxy-phenyl)-3-oxo-propionitrile in the amount of 2.5463 gms.

3-(4-Ethoxy-phenyl)-3-oxo-propionitrile (2.5463 gms.) is then suspended in 55 mL of anhydrous EtOH. This suspension is treated with 0.85 mL of anhydrous hydrazine and subsequently heated to refluxing temperature for 1 day. The reaction mixture is concentrated in vacuo. The residue is then triturated with isopropanol to precipitate out the 5-(4-ethoxy-phenyl)-2H-pyrazol-3-ylamine.

EXAMPLE 39

3-{[5-(3-Methyl-benzyl)-2H-pyrazol-3-ylamino]-methylene}-1,3-dihydro-indol-2-one The named compound is prepared by substituting 5-(3-methyl-benzyl)-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.240 gms. 5-(3-methyl-benzyl)-2H-pyrazol-3-ylamine by refluxing in tetrahydrofuran (2.5 mL) overnight.

5-(3-Methyl-benzyl)-2H-pyrazol-3-ylamine

The named compound is the 3-aminopyrazole used in the reaction of Example 39 and can be prepared from m-tolyl-acetic acid ethyl ester by the following method:

Under Ar$_{(g)}$, a solution of anhydrous acetonitrile (1.5 mL) in 35 mL anhydrous THF is cooled to −78° C. in a dry ice-acetone bath and then slowly treated with 11 mL of a 2.5 M n-butyl lithium in hexanes. The reaction mixture is maintained at −78° C. for an additional 45 min. and then slowly treated with a solution of 5 gms. of m-tolyl-acetic acid ethyl ester in 5 mL of anhydrous THF. The resulting solution is then stirred overnight at room temperature. Subsequently, the reaction mixture is treated with 10% NaOH$_{(aq)}$ to dissolve solids and then extracted with ethyl acetate. The aqueous layer is acidified (pH 6) with HCl$_{(aq)}$ affording a white precipitate which subsequently is filtered. The organic layer is concentrated in vacuo, and the residue is triturated with isopropanol resulting in the formation of additional white precipitate. The combined precipitates provide the desired 3-oxo4-m-tolyl-butyronitrile in the amount of 2.5463 gms.

3-Oxo-4-m-tolyl-butyronitrile (2.5583 gms.) is then suspended in 50 mL of anhydrous EtOH. This suspension is treated with 1.0 mL of anhydrous hydrazine, and subsequently heated to refluxing temperature for 1 day. The reaction mixture is concentrated in vacuo. The residue is then triturated with isopropanol to precipitate out the 5-(3-methylbenzyl)-2H-pyrazol-3-ylamine.

EXAMPLE 40

3-[(5-Benzyl-2H-pyrazol-3-ylamino)-methylene]-1,3-dihydro-indol-2-one

The named compound is prepared by substituting 5-benzyl-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.231 gms. 5-benzyl-2H-pyrazol-3-ylamine by refluxing in tetrahydrofuran (2.5 mL) overnight.

5-Benzyl-2H-pyrazol-3-ylamine

The named compound is the 3-aminopyrazole used in the reaction of Example 40 and can be prepared from phenylacetic acid ethyl ester by the following method:

Under Ar$_{(g)}$, a solution of anhydrous acetonitrile (1.6 mL) in 35 mL anhydrous THF is cooled to −78° C. in a dry ice-acetone bath and then slowly treated with 12.2 mL of a 2.5 M n-butyl lithium in hexanes. The reaction mixture is maintained at −78° C. for an additional 45 min. and then slowly treated with a solution of 5 gms. of phenyl-acetic acid ethyl ester in 5 mL of anhydrous THF. The resulting solution is then stirred overnight at room temperature. Subsequently, the reaction mixture is treated with 10% NaOH$_{(aq)}$ to dissolve solids and then extracted with ethyl acetate. The aqueous layer is acidified (pH 6) with HCl$_{(aq)}$ affording a white precipitate which subsequently is filtered. The organic layer is concentrated in vacuo, and the residue is triturated with isopropanol resulting in the formation of additional white precipitate. The combined precipitates provide the desired 3-oxo-4-phenyl-butyronitrile in the amount of 4.0262 gms.

3-Oxo-4-phenyl-butyronitrile (4.0262 gms.) is then suspended in 75 mL of anhydrous EtOH. This suspension is treated with 1.6 mL of anhydrous hydrazine, and subsequently heated to refluxing temperature for 1 day. The reaction mixture is concentrated in vacuo. The residue is then triturated with isopropanol to precipitate out the 5-benzyl-2H-pyrazol-3-ylamine.

EXAMPLE 41

3-[(5-tert-Butyl-isoxazol-3-ylamino)-methylene]-1,3-dihydro-indol-2-one

The named compound is prepared by substituting 5-tert-butyl-isoxazol-3-ylamine for 3-aminopyrazole in the reaction of Example 1. Specifically, E & Z-3-[(hydroxy)-methylene]-1,3-dihydro-indol-2-one (0.100 gms.) is reacted with 0.1742 gms. 5-tert-butyl-isoxazol-3-ylamine by refluxing in tetrahydrofuran (2.7 mL).

EXAMPLE 42

3-[(4-Bromo-5-methyl-isoxazol-3-ylamino)-methylene]-1,3-dihydro-indol-2-one

The named compound is prepared by substituting 4-bromo-5-methyl-isoxazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2211 gms. 4-bromo-5-methyl-isoxazol-3-ylamine by refluxing in tetrahydrofuran (2.7 mL).

EXAMPLE 43

3-(Isoxazol-3-ylaminomethylene)-1,3-dihydro-indol-2-one

The named compound is prepared by substituting isoxazol-3-ylamine for 3-aminopyrazole in the reaction of Example 1. Specifically, E & Z-3-[(hydroxy)-methylene]-1,3-dihydro-indol-2-one (0.100 gms.) is reacted with 0.09 mL isoxazol-3-ylamine by refluxing in tetrahydrofuran (2.7 mL).

EXAMPLE 44

3-[(5-Methyl-isoxazol-3-ylamino)-methylene]-1,3-dihydro-indol-2-one

The named compound is prepared by substituting 5-methyl-isoxazol-3-ylamine for 3-aminopyrazole in the reaction of Example 1. Specifically, E & Z-3-[(hydroxy)-methylene]-1,3-dihydro-indol-2-one (0.100 gms.) is reacted with 0.1228 gms. 5-methyl-isoxazol-3-ylamine by refluxing in tetrahydrofuran (2.7 mL).

EXAMPLE 45

3-[(3,4-Dimethyl-isoxazol-5-ylamino)-methylene]-1,3-dihydro-indol-2-one

The named compound is prepared by substituting 3,4-dimethyl-isoxazol-5-ylamine for 3-aminopyrazole in the reaction of Example 1. Specifically, E & Z-3-[(hydroxy)-methylene]-1,3-dihydro-indol-2-one (0.100 gms.) is reacted with 0.1388 gms. 3,4-dimethyl-isoxazol-5-ylamine by refluxing in tetrahydrofuran (2.7 mL).

EXAMPLE 46

3-[(2-Ethyl-2H-pyrazol-3-ylamino)-methylene]-1,3-dihydro-indol-2-one

The named compound is prepared by substituting 2-ethyl-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.1632 gms. 2-ethyl-2H-pyrazol-3-ylamine by refluxing in tetrahydrofuran (2.5 mL).

EXAMPLE 47

3-{[5-(5-tert-Butyl-2-methyl-furan-3-yl)-2-methyl-2H-pyrazol-3-ylamino]-methylene}-1,3-dihydro-indol-2-one The named compound is prepared by substituting 5-(5-tert-butyl-2-methyl-furan-3-yl)-2-methyl-2H-pyrazol-3-ylamine for 3-aminopyrazole in the reaction of Example 1. Specifically, E & Z-3-[(hydroxy)-methylene]-1,3-dihydro-indol-2-one (0.100 gms.) is reacted with 0.2377 gms. 5-(5-tert-butyl-2-methyl-furan-3-yl)-2-methyl-2H-pyrazol-3-ylamine by refluxing in tetrahydrofuran (2.5 mL).

EXAMPLE 48

6-Fluoro-3-[(5-methyl-isoxazol-3-ylamino)-methylene]-1,3-dihydro-indol-2-one

The named compound is prepared by substituting E & Z-3-[(hydroxy)-methylene]-6-fluoro-1,3-dihydro-indol-2-one for E & Z-3-[(hydroxy)-methylene]-1,3-dihydro-indol-2-one and 5-methyl-isoxazol-3-ylamine for 3-aminopyrazole in the reaction of Example 1. Specifically, E & Z-3-[(hydroxy)-methylene]-6-fluoro-1,3-dihydro-indol-2-one (0.033 gms.) is reacted with 0.040 gms. 5-methyl-isoxazol-3-ylamine by refluxing in tetrahydrofuran (0.88 mL) to afford the named compound in the amount of 0.0147 gms.

EXAMPLE 49

6-Fluoro-3-[(5-methyl-1H-pyrazol-3-ylamino)-methylene]-1,3-dihydro-indol-2-one

The named compound is prepared by substituting E & Z-3-[(hydroxy)-methylene]-6-fluoro-1,3-dihydro-indol-2-one for E & Z-3-[(hydroxy)-methylene]-1,3-dihydro-indol-2-one and 5-methyl-1H-pyrazol-3-ylamine for 3-aminopyrazole in the reaction of Example 1. Specifically, E & Z-3-[(hydroxy)-methylene]-6-fluoro-1,3-dihydro-indol-2-one (0.033 gms.) is reacted with 0.040 gms. 5-methyl-1H-pyrazol-3-ylamine by refluxing in tetrahydrofuran (0.88 mL) to afford the named compound in the amount of 0.0163 gms.

EXAMPLE 50

6-Fluoro-3-[(5-furan-2-yl-1H-pyrazol-3-ylamino)-methylene]-1,3-dihydro-indol-2-one The named compound is prepared by substituting E & Z-3-[(hydroxy)-methylene]-6-fluoro-1,3-dihydro-indol-2-one for E & Z-3-[(hydroxy)-methylene]-1,3-dihydro-indol-2-one and 5-furan-2-yl-1H-pyrazol-3-ylamine for 3-aminopyrazole in the reaction of Example 1. Specifically, E & Z-3-[(hydroxy)-methylene]-6-fluoro-1,3-dihydro-indol-2-one (0.033 gms.) is reacted with 0.061 gms. 5-furan-2-yl-1H-pyrazol-3-ylamine by refluxing in tetrahydrofuran (0.88 mL) to afford the named compound in the amount of 0.0263 gms.

EXAMPLE 51

6-Fluoro-3-[(5-phenyl-1H-pyrazol-3-ylamino)-methylene]-1,3-dihydro-indol-2-one

The named compound is prepared by substituting E & Z-3-[(hydroxy)-methylene]-6-fluoro-1,3-dihydro-indol-2-one for E & Z-3-[(hydroxy)-methylene]-1,3-dihydro-indol-2-one and 5-phenyl-1H-pyrazol-3-ylamine for 3-aminopyrazole in the reaction of Example 1. Specifically, E & Z-3-[(hydroxy)-methylene]-6-fluoro-1,3-dihydro-indol-2-one (0.033 gms.) is reacted with 0.065 gms. 5.-phenyl-1H-pyrazol-3-ylamine by refluxing in tetrahydrofuran (0.88 mL) to afford the named compound in the amount of 0.0417 gms.

EXAMPLE 52

3-{[5-(5-tert-Butyl-2-methyl-furan-3-yl)-2H-pyrazol-3-ylamino]-methylene}-6-fluoro-1,3-dihydro-indol-2-one The named compound is prepared by substituting E & Z-3-[(hydroxy)-methylene]-6-fluoro-1,3-dihydro-indol-2-one for E & Z-3-[(hydroxy)-methylene]-1,3-dihydro-indol-2-one and 5-(5-tert-butyl-2-methyl-furan-3-yl)-2H-pyrazol-3-ylamine for 3-aminopyrazole in the reaction of Example 1. Specifically, E & Z-3-[(hydroxy)-methylene]-6-fluoro-1,3-dihydro-indol-2-one (0.033 gms.) is reacted with 0.089 gms. 5-(5-tert-butyl-2-methyl-furan-3-yl)-2H-pyrazol-3-ylamine by refluxing in tetrahydrofuran (0.88 mL) to afford the named compound in the amount of 0.0362 gms.

EXAMPLE 53

3-{[5-(5-tert-Butyl-2-methyl-furan-3-yl)-2H-pyrazol-3-ylamino]-methylene}-6-fluoro-1,3-dihydro-indol-2-one The named compound is prepared by substituting E & Z-3-[(hydroxy)-methylene]-6-fluoro-1,3-dihydro-indol-2-one for E & Z-3-[(hydroxy)-methylene]-1,3-dihydro-indol-2-one in the reaction of Example 1. Specifically, E & Z-3-[(hydroxy)-methylene]-6-fluoro-1,3-dihydro-indol-2-one (0.033 gms.) is reacted with 0.034 gms. 3-aminopyrazole by refluxing in tetrahydrofuran (0.88 mL) to afford the named compound in the amount of 0.0184 gms.

EXAMPLE 54

3-{5-(4-Methoxy-benzyl)-1H-pyrrol-3-ylamino]-methylene]-4-methyl-1,3-dihydro-indol-2-one The named compound is prepared by substituting E & Z-3-[(hydroxy)-methylene]-4-methyl-1,3-dihydro-indol-2-one for E & Z-3-[(hydroxy)-methylene]-1,3-dihydro-indol-2-one and 5-(4-methoxy-benzyl)-1H-pyrazol-3-ylamine (see Example 5) for 3-aminopyrazole in the reaction of Example 1. Specifically, E & Z-3-[(hydroxy)-methylene]-4-methyl-1,3-dihydro-indol-2-one (0.045 gms.) is reacted with 0.078 gms. of 5-(4-methoxy-benzyl)-1H-pyrazol-3-ylamine by refluxing in tetrahydrofuran (2.5 mL).

EXAMPLE 55

6-Fluoro-3-{5-(4-Methoxy-benzyl)-1H-pyrrol-3-ylamino]-methylene]-1,3-dihydro-indol-2-one The named compound is prepared by substituting E & Z-3-[(hydroxy)-methylene]-6-fluoro-1,3-dihydro-indol-2-one for E & Z-3-[(hydroxy)-methylene]-1,3-dihydro-indol-2-one and 5-(4-methoxy-benzyl)-1H-pyrazol-3-ylamine (see Example 5) for 3-aminopyrazole in the reaction of Example 1. Specifically, E & Z-3-[(hydroxy)-methylene]-4-methyl-1,3-dihydro-indol-2-one (0.046 gms.) is reacted with 0.078 gms. of 5-(4-methoxy-benzyl)-1H-pyrazol-3-ylamine by refluxing in tetrahydrofuran (2.5 mL).

EXAMPLE 56

3-({5-[4-(3-Dimethylamino-propoxy)-benzyl]-2H-pyrazol-3-ylamino]-methylene)-1,3-dihydro-indol-2-one The named compound is prepared by substituting 5-[4-(3-dimethylamino-propoxy)-benzyl]-2H-pyrazol-3-ylamine for 3-aminopyrazole in the reaction of Example 1. Specifically, E & Z-3-[(hydroxy)-methylene]-1,3-dihydro-indol-2-one (0.0351 gms.) is reacted with 0.0881 gms. of 5-[4-(3-dimethylamino-propoxy)-benzyl]-2H-pyrazol-3-ylamine by refluxing in tetrahydrofuran (2.0 mL). Recrystallization from a mixture of ethyl acetate and hexanes affords the named compound.

EXAMPLE 57

3-({5-[4-(3-Dimethylamino-propoxy)-benzyl]-2H-pyrazol-3-ylamino]-methylene)-1,3-dihydro-indol-2-one The named compound is prepared by substituting E & Z-3-[(hydroxy)-methylene]-4-methyl-1,3-dihydro-indol-2-one for E & Z-3-[(hydroxy)-methylene]-1,3-dihydro-indol-2-one and 5-[4-(3-dimethylamino-propoxy)-benzyl]-2H-pyrazol-3-ylamine for 3-aminopyrazole in the reaction of Example 1. Specifically, E & Z-3-[(hydroxy)-methylene]-4-methyl-1,3-dihydro-indol-2-one (0.0351 gms.) is reacted with 0.0881 gms. of 5-[4-(3-dimethylamino-propoxy)-benzyl]-2H-pyrazol-3-ylamine by refluxing in tetrahydrofuran (2.0 mL). Recrystallization from a mixture of ethyl acetate and hexanes affords the named compound.

5-[4-(3-Dimethylamino-propoxy)-benzyl]-2H-pyrazol-3-ylamine

The named compound is the 3-aminopyrazole used in the reactions of Examples 56 and 57, and can be prepared from (4-hydroxy-phenyl)-acetic acid ethyl ester by the following method:

Under $Ar_{(g)}$, (3-Chloro-propyl)-dimethyl-amine hydrochloride (8.0 gms.), ethyl 4-hydroxyphenyl acetate (4.5 gms.) and anhydrous potassium carbonate (13.8 gms.) are suspended in 200 mL of DMF. The reaction mixture is heated to 60° C. overnight (~16 h) then cooled to room temperature and filtered through a plug of silica gel. The filtrate is concentrated in vacuo, diluted with ethyl acetate and extracted with water. The aqueous layer is then re-extracted twice with ethyl acetate. The organic layers are combined, dried over anhydrous $Na_2SO_4$ and concentrated in vacuo affording a dark brown oil. The crude oil was purified using flash silica gel chromatography (100% ethyl acetate as eluant) affording the desired alkylation product, [4-(3-dimethylamino-propxy)-phenyl]-acetic acid ethyl ester, as a light brown oil (42% yield).

The [4-(3-Dimethylamino-propxy)-phenyl]-acetic acid ethyl ester is then condensed with the lithium anion of acetonitrile by the following method: A solution of dry acetonitrile (0.627 mL) in 20 mL of THF, that had been cooled in a dry ice-acetone bath for 2 h under $Ar_{(g)}$, is treated dropwise with 6 mL of a 2M solution of n-butyl lithium in cyclohexane. This mixture is allowed to stir at −78° C. for an additional 1.5 h, and is subsequently treated with 2.45 gms. of [4-(3-dimethylamino-propoxy)-phenyl]-acetic acid ethyl ester in dropwise fashion. The resulting solution is allowed to stir at −78° C. for an additional 30 minutes, and is then allowed to warm to room temperature overnight. The reaction mixture is then vacuum filtered affording the desired nitrile, 4-[4-(3-dimethylamino-propoxy)-phenyl]-3-oxo-butyronitrile, as a white solid (20-28% yield).

The 4-[4-(3-dimethylamino-propoxy)-phenyl]-3-oxo-butyronitrile is then converted to the appropriate aminopyrazole by the following method: Under $Ar_{(g)}$, 0.285 gms. of the 4-[4-(3-dimethylamino-propoxy)-phenyl]-3-oxo-butyronitrile is dissolved in 5 mL of anhydrous EtOH and then is treated with 0.100 mL anhydrous hydrazine. The reaction mixture is then heated overnight at 65° C., subsequently, cooled to room temperature and concentrated in vacuo providing 5-[4-(3-dimethylamino-propoxy)-benzyl]-2H-pyrazol-3-ylamine which is use in crude form in the reactions of Examples 56 and 57.

EXAMPLE 58

3-({5-[4-(3-Morpholin-4-yl-propoxy)-benzyl]-2H-pyrazol-3-ylamino}-methylene)-1,3-dihydro-indol-2-one The named compound is prepared by substituting 5-[4-(3-morpholin-4-yl-propoxy)-benzyl]-2H-pyrazol-3-ylamine for 3-aminopyrazole in the reaction of Example 1. Specifically, E & Z-3-[(hydroxy)-methylene]-1,3-dihydro-indol-2-one (0.017 gms.) is reacted with 0.048 gms. of 5-[4-(3-morpholin-4-yl-propoxy)-benzyl]-2H-pyrazol-3-ylamine by refluxing in tetrahydrofuran (1.0 mL). Recrystallization from a mixture of ethyl acetate and hexanes affords the named compound.

5-[4-(3-Morpholin-4-yl-propoxy)-benzyl]-2H-pyrazol-3-ylamine

The named compound is the 3-aminopyrazole used in the reaction of Example 58, and can be prepared from (4-hydroxy-phenyl)-acetic acid ethyl ester by the following method:

Under $Ar_{(g)}$, 6.99 gms. of 1-bromo-3-chloropropane, 4.52 gms. of ethyl 4-hydroxyphenyl acetate and 9.22 gms. of anhydrous potassium carbonate are suspended in 150 mL of DMF. The resulting mixture is heated overnight (~16 h) at 60° C. and, subsequently, is cooled to room temperature and filtered through a plug of silica gel. The filtrate is concentrated in vacuo, diluted with ethyl acetate and extracted with water. The aqueous layer is then re-extracted twice with ethyl acetate. The organic layers are combined, dried over anhydrous $Na_2SO_4$ and concentrated in vacuo to afford a black oil. Following purification by flash silica gel chromatography (1:1 ethyl acetate:hexanes as eluant) the desired [4-(3-bromo-propoxy)-phenyl]-acetic acid ethyl ester is isolated as a amber colored oil.

The [4-(3-bromo-propoxy)-phenyl]-acetic acid ethyl ester (1.90 gms.) is condensed with morpholine (0.645 g, 8.88 mmol) in 7.4 mL of THF overnight at 65° C. Subsequently, the reaction mixture is diluted with ethyl acetate and extracted with water. The aqueous layer is then re-extracted twice with ethyl acetate. The organic layers are combined, dried over anhydrous $Na_2SO_4$ and concentrated in vacuo affording a crude brown oil (55% yield). Following purification by flash silica gel chromatography (100% ethyl acetate as eluant) the desired [4-(3-morpholin-4-yl-propoxy)-phenyl]-acetic acid ethyl ester is isolated cleanly as an oil.

The [4-(3-morpholin-4-yl-propoxy)-phenyl]-acetic acid ethyl ester is then condensed with the lithium anion of acetonitrile by the following method: A solution of dry acetonitrile (0.254 mL) in 5 mL of THF, that had been cooled in a dry ice-acetone bath for 2 h under $Ar_{(g)}$, is treated dropwise with 2.43 mL of a 2M solution of n-butyl lithium in cyclohexane. This mixture is allowed to stir at −78° C. for an additional 1.5 h, and is subsequently treated with 1.15 gms. of [4-(3-morpholin-4-yl-propoxy)-phenyl]-acetic acid ethyl ester in dropwise fashion. The resulting solution is allowed to stir at −78° C. for an additional 30 minutes, and is then allowed to warm to room temperature overnight. The reaction mixture, subsequently, is vacuum filtered affording the desired nitrile, 4-[4-(3-morpholin-4-yl-propoxy)-phenyl]-3-oxo-butyronitrile, as a white solid (11% yield).

The 4-[4-(3-morpholin-4-yl-propoxy)-phenyl]-3-oxo-butyronitrile is then converted to the appropriate aminopyrazole by the following method: Under $Ar_{(g)}$, 0.095 gms. of the 4-[4-(3-morpholin-4-yl-propoxy)-phenyl]-3-oxo-butyronitrile is dissolved in 2 mL of anhydrous EtOH and then is treated with 0.100 gms. anhydrous hydrazine. The reaction mixture is then heated overnight at 65° C., subsequently, cooled to room temperature and concentrated in vacuo providing 5-[4-(3-morpholin-4-yl-propoxy)-benzyl]-2H-pyrazol-3-ylamine which is use in crude form in the reaction of Example 58.

Thus, by means of the above examples, the following compounds are synthesized:

3-[(1-H-Pyrazol-3ylamino)-methylene]1,3-dihydro-indol-2-one
3-[(5-Phenyl-1H-pyrazol-3-ylamino)-methylene]-1,3-dihydro-indol-2-one
3-[(5-P-Tolyl-1H-pyrazol-3-ylamino)-methylene]-1,3-dihydro-indol-2-one
3-[(5-Furan-2-yl-1H-pyrazol-3-ylamino)-methylene]-1,3-dihydro-indol-2-one
3-{[5-(4-Methoxy-benzyl)-1H-pyrazol-3-ylamino]-methylene}-1,3-dihydro-indol-2-one
4-Methyl-3-[(1H-pyrazol-3-ylamino)-methylene]-1,3-dihydro-indol-2-one
3-[(5-Furan-2-yl-1H-pyrazol-3-ylamino)-methylene]-4-methyl-1,3-dihydro-indol-2-one
4-Methyl-3-[(5-phenyl-1H-pyrazol-3-ylamino)-methylene-1,3-dihydro-indol-2-one
3-(5-Chloro-2-oxo-1,2-dihydro-indol-3-ylidenemethylamino)pyrazole
3-(5-Chloro-2-oxo-1,2-dihydro-indol-3-ylidenemethylamino)-5-f(2-furyl)pyrazole
3-[(4-Bromo-5-phenyl-1H-pyrazol-3-ylamino)-methylene]-1,3-dihydro-indol-2-one
3-[(4-Bromo-5-phenyl-1H-pyrazol-3-ylamino)-methylene]-4-methyl-1,3-dihydro-indol-2-one
3-[(4-Bromo-5-phenyl-1H-pyrazol-3-ylamino)-methylene]-5-chloro-1,3-dihydro-indol-2-one
5-Chloro-3-[(5-phenyl-1H-pyrazol-3-ylamino)-methylene]-1,3-dihydro-indol-2-one
3-[(4-Fluoro-1H-indazol-3-ylamino)-methylene]-1,3-dihydro-indol-2-one
3-[(2-Oxo-1,2-dihydro-indol-3-ylidenemethyl)-amino]-1H-pyrazole-4-carboxylic acid ethyl ester
5-Methylsulfanyl-3-[(2-oxo-1,2-dihydro-indol-3-ylidenemethyl)-amino]-1H-pyrazole-4-carbonitrile
3-[(2-Oxo-1,2-dihydro-indol-3-ylidenemethyl)-amino]-1H-pyrazole-4-carboxylic acid
3-[(2-Oxo-1,2-dihydro-indol-3-ylidenemethyl)-amino]-1H-pyrazole-4-carbonitrile
3-[(4-Bromo-1H-pyrazol-3-ylamino)-methylene]-1,3-dihydro-indol-2-one
3-[(5-tert-Butyl-1H-pyrazol-3-ylamino)-methylene]-1,3-dihydro-indol-2-one
3-[(5-Methyl-1H-pyrazol-3-ylamino)-methylene]-1,3-dihydro-indol-2-one
4-{5-[(2-Oxo-1,2-dihydro-indol-3-ylidenemethyl)-amino]-2H-pyrazol-3-yl}-benzoic acid methyl ester
3-[(4,6-Dimethyl-1H-pyrazolo[3,4-b]pyridin-3-ylamino)-methylene]-1,3-dihydro-indol-2-one
5-Fluoro-3-[(5-methyl-1H-pyrazol-3-ylamino)-methylene]-1,3-dihydro-indol-2-one
5-Fluoro-3-[(5-furan-2-yl-1H-pyrazol-3-ylamino)-methylene]-1,3-dihydro-indol-2-one
3-{[5-(5-tert-Butyl-2-methyl-furan-3-yl)-1H-pyrazol-3-ylamino]-methylene}-5-fluoro-1,3-dihydro-indol-2-one
3-{[4-(3,4-Dimethoxy-phenyl)-5-methyl-2H-pyrazol-3-ylamino]-methylene}-1,3-dihydro-indol-2-one
3-{[5-(5-tert-Butyl-2-methyl-furan-3-yl)-2H-pyrazol-3-ylamino]-methylene}-1,3-dihydro-indol-2-one
3-{[5-(4-Methoxy-phenyl)-2H-pyrazol-3-ylamino]-methylene}-1,3-dihydro-indol-2-one
3-{[5-(3,5-Bis-benzyloxy-phenyl)-2H-pyrazol-3-ylamino]-methylene}-1,3-dihydro-indol-2-one
3-{[5-(3,5-Dimethyl-phenyl)-2H-pyrazol-3-ylamino]-methylene}-1,3-dihydro-indol-2-one
3-{[5-(3-Methoxy-phenyl)-2H-pyrazol-3-ylamino]-methylene}-1,3-dihydro-indol-2-one
3-{[5-(2,4-Dimethyl-phenyl)-2H-pyrazol-3-ylamino]-methylene}-1,3-dihydro-indol-2-one
3-{[5-(4-Dimethylamino-phenyl)-2H-pyrazol-3-ylamino]-methylene}-1,3-dihydro-indol-2-one
3-{[5-(2,3,5-Trimethyl-benzyl)-2H-pyrazol-3-ylamino]-methylene}-1,3-dihydro-indol-2-one
3-{[5-(2-Methoxy-phenyl)-2H-pyrazol-3-ylamino]-methylene}-1,3-dihydro-indol-2-one
3-{[5-(4-Ethoxy-phenyl)-2H-pyrazol-3-ylamino]-methylene}-1,3-dihydro-indol-2-one
3-{[5-(3-Methyl-benzyl)-2H-pyrazol-3-ylamino]-methylene-1,3-dihydro-indol-2-one
3-[(5-Benzyl-2H-pyrazol-3-ylamino)-methylene]-1,3-dihydro-indol-2-one
3-[(5-tert-Butyl-isoxazol-3-ylamino)-methylene]-1,3-dihydro-indol-2-one
3-[(4-Bromo-5-methyl-isoxazol-3-ylamino)-methylene-1,3-dihydro-indol-2-one
3-(Isoxazol-3-ylaminomethylene)-1,3-dihydro-indol-2-one
3-[(5-Methyl-isoxazol-3-ylamino)-methylene]-1,3-dihydro-indol-2-one
3-[(3,4-Dimethyl-isoxazol-5-ylamino)-methylene]-1,3-dihydro-indol-2-one
3-[(2-Ethyl-2H-pyrazol-3-ylamino)-methylene]-1,3-dihydro-indol-2-one
3-{[5-(5-tert-Butyl-2-methyl-furan-3-yl)-2-methyl-2H-pyrazol-3-ylamino]-methylene}-1,3-dihydro-indol-2-one
6-Fluoro-3-[(5-methyl-isoxazol-3-ylamino)-methylene]-1,3-dihydro-indol-2-one
6-Fluoro-3-[(5-methyl-1H-pyrazol-3-ylamino)-methylene]-1,3-dihydro-indol-2-one
6-Fluoro-3-[(5-furan-2-yl-1H-pyrazol-3-ylamino)-methylene]-1,3-dihydro-indol-2-one
6-Fluoro-3-[(5-phenyl-1H-pyrazol-3-ylamino)-methylene]-1,3-dihydro-indol-2-one
3-{[5-(-tert-Butyl-2-methyl-furan-3-yl)-2H-pyrazol-3-ylamino]-methylene}-6-fluoro-1,3-dihydro-indol-2-one
6-Fluoro-3-[(1H-pyrazol-3-ylamino)-methylene]-1,3-dihydro-indol-2-one
3-{5-(4-Methoxy-benzyl)-1H-pyrrol-3-ylamino]-methylene}-4-methyl-1,3-dihydro-indol-2-one
6-Fluoro-3-{5-(4-Methoxy-benzyl)-1H-pyrrol-3-ylamino]-methylene}-1,3-dihydro-indol-2-one 3-({5-[4-(3-Dimethylamino-propoxy)-benzyl)-2H-pyrazol-3-ylamino]-methylene]-1,3-dihydro-indol-2-one
3-({5-[4-(3-Dimethylamino-propoxy)-benzyl)-2H-pyrazol-3-ylamino]-methylene]-4-methyl-1,3-dihydro-indol-2-one
3-({5-[4-(3Morpholin-4-yl-propoxy)-benzyl]-2H-pyrazol-3-yl-amino}-methylene)-1,3-dihydro-indol-2-one
3-({5-[4-(3-Dimethylamino-propoxy)-benzyl]-2H-pyrazol-3-ylamino}-methylene)-5-fluoro-1,3-dihydro-indol-2-one
5-Chloro-3-({5-[4-(3-dimethylamino-propoxy)-benzyl]-2H-pyrazol-3-ylamino}-methylene)-1,3-dihydro-indol-2-one
3-({5-[4-(3-Dimethylamino-propoxy)-benzyl]-2H-pyrazol-3-ylamino}-methylene)-6-fluoro-1,3-dihydro-indol-2-one
6-Fluoro-3-({5-[4-(3-morpholin-4-yl-propoxy)-benzyl]-2H-pyrazol-3-ylamino}-methylene)-1,3-dihydro-indol-2-one
4-Methyl-3-({5-[4-(3-morpholin-4-yl-propoxy)-benzyl]-2H-pyrazol-3-ylamino}-methylene)-1,3-dihydro-indol-2-one
5-Fluoro-3-({5-[4-(3-morpholin-4-yl-propoxy)-benzyl]-2H-pyrazol-3-ylamino}-methylene)-1,3-dihydro-indol-2-one
5-Chloro-3-({5-[4-(3-morpholin-4-yl-propoxy)-benzyl]-2H-pyrazol-3-ylamino}-methylene)-1,3-dihydro-indol-2-one
3-[(5-{4-[3-(4-Methyl-piperazin-1-yl)-propoxy]-benzyl}-2H-pyrazol-3-ylamino)-methylene]-1,3-dihydro-indol-2-one
4-Methyl-3-[(5-{4-[3-(4-methyl-piperazin-1-yl)-propoxy]-benzyl}-2H-pyrazol-3-ylamino)-methylene]-1,3-dihydro-indol-2-one
6-Fluoro-3-[(5-{4-[3-(4-methyl-piperazin-1-yl)-propoxy]-benzyl}-2H-pyrazol-3-ylamino)-methylene]-1,3-dihydro-indol-2-one
5-Fluoro-3-[(5-{4-[3-(4-methyl-piperazin-1-yl)-propoxy]-benzyl}-2H-pyrazol-3-ylamino)-methylene]-1,3-dihydro-indol-2-one
5-Chloro-3-[(5-{4-[3-(4-methyl-piperazin-1-yl)-propoxy]-benzyl}-2H-pyrazol-3-ylamino)-methylene]-1,3-dihydro-indol-2-one The present invention is not to be limited in scope by the exemplified embodiments which are intended as illustrations of single aspects of the invention only. Indeed, various modifications of the invention in addition to those described herein will become apparent to those skilled in the art from the foregoing description. For example novel compounds of formula II, below may be utilized in the method of treating diseases described above.

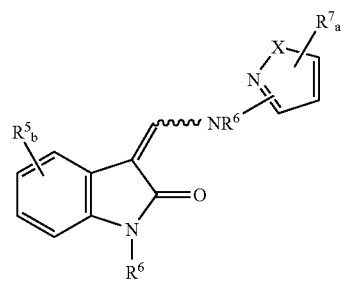

wherein $R^5$ is selected from the group consisting of halogen, nitro, hydroxy, hydrocarbyl, substituted hydrocarbyl, amide, thioamide, amine, thioether and sulfonyl; X is selected from the group consisting of $NR^6$ and O; $R^7$ is selected from the group consisting of nitro, hydroxy, hydrocarbyl, substituted hydrocarbyl, amide, thioamide, amine, thioether and sulfonyl and phosphonic acid; $R^6$ is selected from the group consisting of hydrogen, hydrocarbyl and substituted hydrocarbyl; b is 0 or an integer from 1 to 3; a is 0 or an integer of from 1 to 3; the wavy line represents a E or Z bond and pharmaceutically acceptable salts thereof. Said hydrocarbyl and/or substituted hydrocarbyl may be alkyl, alkenyl, alkynyl, aryl (including carbocylic aryl and heterocyclic aryl) and alkaryl.

Such modifications are intended to fall within the scope of the appended claims.

All references cited herein are hereby incorporated by reference in their entirety.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:

1. A compound represented by the formula:

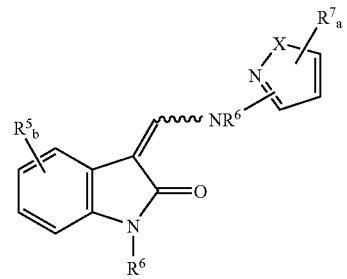

wherein $R^5$ is selected from the group consisting of halogen, nitro, hydroxy, hydrocarbyl, substituted hydrocarbyl, amide, thioamide, amine, thioether and sulfonyl; X is O; $R^7$ is selected from the group consisting of halogen, nitro, hydroxy, hydrocarbyl, substituted hydrocarbyl, amide, thioamide, amine, thioether and sulfonyl and phosphonic acid; $R^6$ is selected from the group consisting of hydrogen, hydrocarbyl and substituted hydrocarbyl; b is 0 or an integer from 1 to 3; a is 0 or an integer of from 1 to 3; the wavy line represents a E or Z bond and pharmaceutically acceptable salts thereof.

2. A method for treating arthritis and psoriasis, the method comprising the step of administering to a subject in need thereof a therapeutically effective amount of the compound of claim 1.

* * * * *

UNITED STATES PATENT AND TRADEMARK OFFICE
CERTIFICATE OF CORRECTION

PATENT NO. : 7,393,870 B2
APPLICATION NO. : 11/282044
DATED : July 1, 2008
INVENTOR(S) : Andrews et al.

It is certified that error appears in the above-identified patent and that said Letters Patent is hereby corrected as shown below:

On the Title Page, in field (56) under "Other Publications" column 2, line 22, delete "In Ovo" and insert -- In Vivo --, therefor.

In column 1, lines 53-60, delete "These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors." and insert the same on line 52 after "profiles." as continuation of paragraph.

In column 4, lines 3-6, delete " 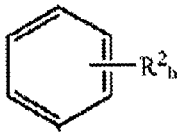 " and insert -- 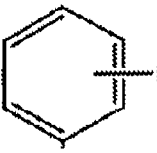 --, therefor.

In column 5, line 32, delete "Pb" and insert -- Ph --, therefor.

In column 10, line 31, after "also" delete "a" and insert -- an --, therefor.

In column 12, line 8, delete "of0" and insert -- of 0 --, therefor.

In column 15, line 51, delete "butyronitile" and insert -- butyronitrile --, therefor.

In column 15, line 52, delete "anydrous" and insert -- anhydrous --, therefor.

In column 19, line 50, delete "anydrous" and insert -- anhydrous --, therefor.

UNITED STATES PATENT AND TRADEMARK OFFICE
CERTIFICATE OF CORRECTION

PATENT NO. : 7,393,870 B2
APPLICATION NO. : 11/282044
DATED : July 1, 2008
INVENTOR(S) : Andrews et al.

It is certified that error appears in the above-identified patent and that said Letters Patent is hereby corrected as shown below:

In column 21, line 12, delete "anydrous" and insert -- anhydrous --, therefor.

In column 22, line 33, delete "filtered" and insert -- filtered. --, therefor.

In column 27, line 12, delete "3-Oxo4" and insert -- 3-oxo-4 --, therefor.

In column 29, line 65, delete "5.-phenyl" and insert -- 5-phenyl --, therefor.

In column 30, line 39, before "5" insert -- [ --

In column 30, line 40, delete "methylene]" and insert -- methylene} --

In column 30, line 55, before "5" insert -- [ --

In column 30, line 56, delete "ethylene]" and insert -- ethylene} --

In column 34, line 35, delete "3-{" and insert -- 3-[ --

In column 34, line 50, after "{" insert -- [ --

In column 34, line 64, after "{" insert -- [ --

In column 34, line 65, delete "ene]" and insert -- ene} --

In column 34, line 66, after "{" insert -- [ --

In column 34, line 67, delete "methylene]" and insert -- methylene} --

In column 35, line 1, after "{" insert -- [ --

In column 35, line 2, delete "methylene]" and insert -- methylene} --

In column 35, line 3, after "{" insert -- [ --

UNITED STATES PATENT AND TRADEMARK OFFICE
CERTIFICATE OF CORRECTION

PATENT NO. : 7,393,870 B2  Page 3 of 3
APPLICATION NO. : 11/282044
DATED : July 1, 2008
INVENTOR(S) : Andrews et al.

It is certified that error appears in the above-identified patent and that said Letters Patent is hereby corrected as shown below:

In column 35, line 4, delete "methylene]" and insert -- methylene} --

Signed and Sealed this

Fourth Day of November, 2008

JON W. DUDAS
*Director of the United States Patent and Trademark Office*